US008367626B2

(12) United States Patent
Furgeson et al.

(10) Patent No.: US 8,367,626 B2
(45) Date of Patent: Feb. 5, 2013

(54) ELASTIN-LIKE POLYMER DELIVERY VEHICLES

(75) Inventors: Darin Y. Furgeson, Sun Prairie, WI (US); Younsoo Bae, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1607 days.

(21) Appl. No.: 11/747,759

(22) Filed: May 11, 2007

(65) Prior Publication Data
US 2007/0265197 A1 Nov. 15, 2007

Related U.S. Application Data

(60) Provisional application No. 60/799,798, filed on May 12, 2006, provisional application No. 60/832,455, filed on Jul. 21, 2006.

(51) Int. Cl.
*A61K 48/00* (2006.01)
(52) U.S. Cl. .................................................. 514/44 R
(58) Field of Classification Search .................. None
See application file for complete search history.

(56) References Cited

U.S. PATENT DOCUMENTS

| 6,852,834 | B2 | 2/2005 | Chilkoti | 530/350 |
|---|---|---|---|---|
| 2005/0255554 | A1 | 11/2005 | Chilkoti | 435/69.1 |

FOREIGN PATENT DOCUMENTS

| WO | WO 2006/001806 | 1/2006 |
|---|---|---|
| WO | WO 2006/042310 | 4/2006 |
| WO | WO 2007/090094 | 8/2007 |

OTHER PUBLICATIONS

Chen, T.H. et al., "Intelligent biosynthetic nanobiomaterials (IBNs) for hyperthermic gene delivery", Mar. 2008, Pharm. Res., vol. 25: pp. 683-691.*
Megeed, Z. et al. "In vitro and in vivo evaluation of recombinant silk-elastinlike hydrogels for cancer gene therapy", 2004, J. Con. Release, vol. 94: pp. 433-445.*
"Correlation of EM diameter with molecular weight", Oct. 2009, one page, TSI Inc.*
Bidwell and Raucher, "Application of thermally responsive polypeptides directed against c-Myc transcriptional function for cancer therapy," *Mol. Cancer Ther.*, 4(7):1076-1085, 2005.
Dreher et al., "Evaluation of an elastin-like polypeptide-doxorubicin conjugate for cancer therapy," *J. Control Release*, 91(1-2):31-43, 2003.
Falk and Issels, "Hyperthermia in oncology," *Int. J. Hyperthermia*, 17:1-18, 2001.
Friedl et al., "Augmentation of endothelial cell monolayer permeability by hyperthermia but not tumor necrosis factor: evidence for disruption of vascular integrity via VE-cadherin down-regulation," *Int. J. Oncol.*, 23:611-616, 2003.
Furgeson et al., "Structural optimization of 'smart' doxoruubicin-polypeptide conjugates for thermally targeted delivery to solid tumors," *J. Control Release*, 110:362-369, 2006.
Furgeson, "Recombinant Elastin Biopolymers for Thermo-Targeted Cancer Therapy," UW-AAPS Student Chapter Presentation, May 3, 2006.
Haider et al., "Molecular engineering of silk-elastinlike polymers for matrix-mediated gene delivery: biosynthesis and characterization," *Mol. Pharm.*, 2:139-150, 2005.
Herrero-Vanrell et al., "Self-assembled particles of an elastin-like polymer as vehicles for controlled drug release," *J. Control Release*, 102(1):113-122, 2005.
Jeon et al., "Thermosensitive Elastin Biopolymers for Systemic Cancer Gene Therapy." 33rd Annual Meeting and Exposition of the Controlled Release Society, Vienna, Austria, Jul. 22-26, 2006.
Kataoka et al., "Block copolymer micelles for drug delivery: design, characterization and biological significance," *Adv. Drug Deliv. Rev.*, 47:113-131, 2001.
Kim et al., "Preparation of poly(ethylene glycol)-block-poly(caprolactone) copolymers and their applications as thermosensitive materials," *J. Biomed. Mater Res. A*, 70(1):154-158, 2004.
Kopecek, "Smart and genetically engineered biomaterials and drug delivery systems," *Eur. J. Pharm. Sci.*, 20(1):1-16, 2003.
Li et al., "The molecular basis for the inverse temperature transition of elastin," *J. Mol. Biol.*, 305:581-592, 2001.
Matsumura and Maeda, "A new concept for macromolecular therapeutics in cancer chemotherapy: mechanism of tumoritropic accumulation of proteins and the antitumor agent smancs.," *Cancer Res.*, 46:6387-6392, 1986.
Meyer and Chilkoti, "Genetically encoded synthesis of protein-based polymers with precisely specified molecular weight and sequence by recursive directional ligation: examples from the elastin-like polypeptide system," *Biomacromolecules*, 3:357-367, 2002.
Sosnik and Cohn, "Reverse thermo-responsive poly(ethylene oxide) and poly(propylene oxide) multiblock copolymers," *Biomaterials*, 26(4):349-357, 2005.
Urry et al., "Biocompatibility of the Bioelastic Materials, Poly(GVGVP) and Its gamma-Irradiation Cross-Linked Matrix: Summary of Genetic Biological Test Results," *J. Bioact. Compat. Polym.*, 6(3):263-282, 1991.
Urry et al., "Physical Chemistry of Biological Free Energy Transduction As Demonstrated by Elastic Protein-Based Polymers," *J. Phys. Chem. B*, 101:11007-11028, 1997.
Yamauchi et al., "Thermoreversible Polyesters Consisting of Multiple Hydrogen Bonding (MHB)," *Macromolecules*, 37(10):3519-3522, 2004.
PCT International Search Report and Written Opinion, issued in International Application No. PCT/US2007/06880, dated Aug. 21, 2008.
Janin, "Heat shock protein 90 inhibitors. A text book example of medicinal chemistry?" *Journal of Medicinal Chemistry*, 48:7503-7512, 2005.
Massodi et al., "Evaluation of cell penetrating peptides fused to elastin-like polypeptide for drug delivery," *Journal of Controlled Release*, 108:396-408, 2005.

* cited by examiner

*Primary Examiner* — Michael Burkhart
(74) *Attorney, Agent, or Firm* — Parker Highlander PLLC

(57) ABSTRACT

In invention concerns elastin-like polymer (ELP) delivery compositions and methods for the use thereof. In some aspects ELP compositions may be used to deliver therapeutic nucleic acids, polypeptides of small molecules. In some aspects, in vivo delivery with ELP compositions can directed to specific target sites by the application of local hyperthermia therapy. Compositions and methods for ELP gene therapy are provided.

36 Claims, 8 Drawing Sheets

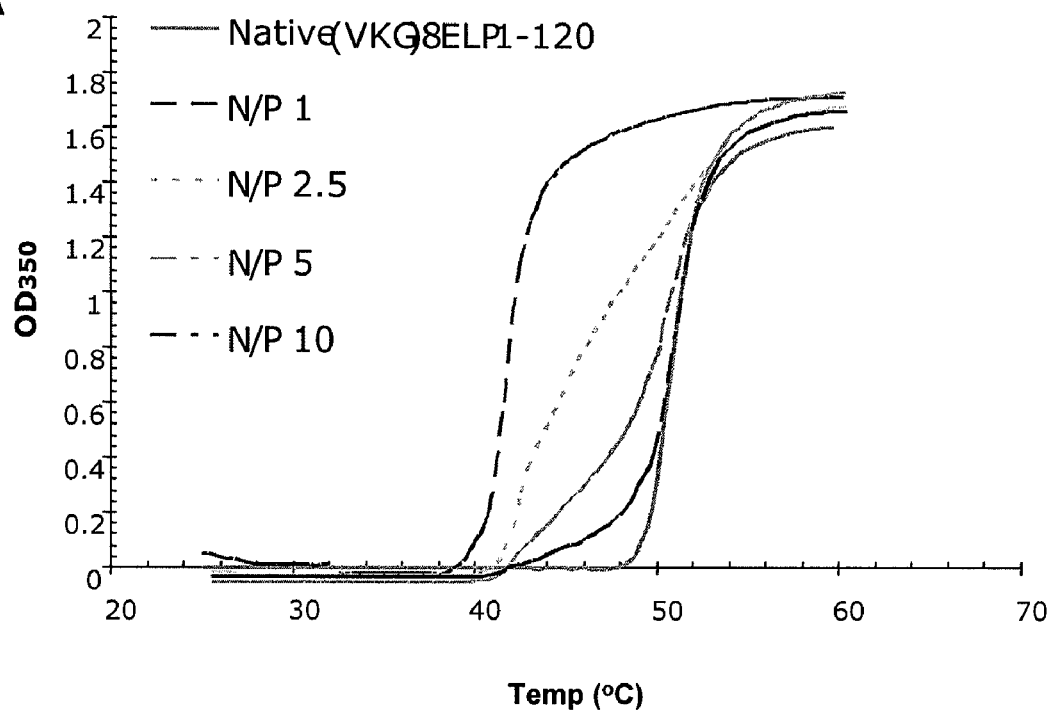
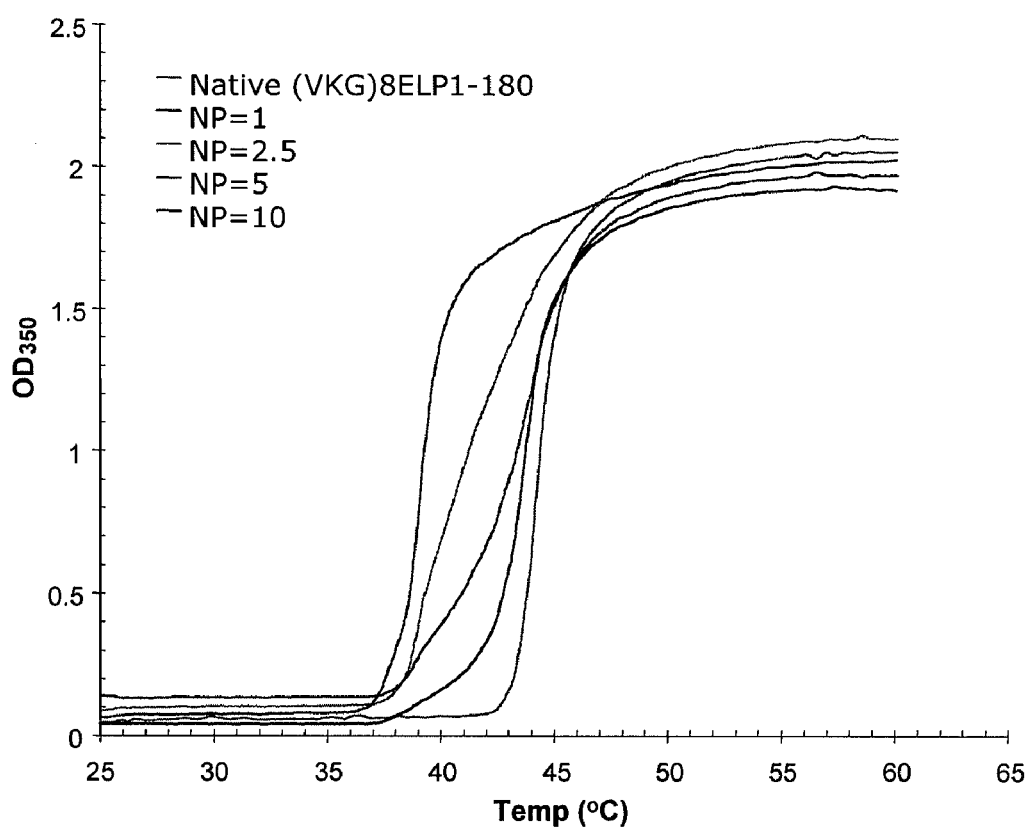
FIG. 4A-B

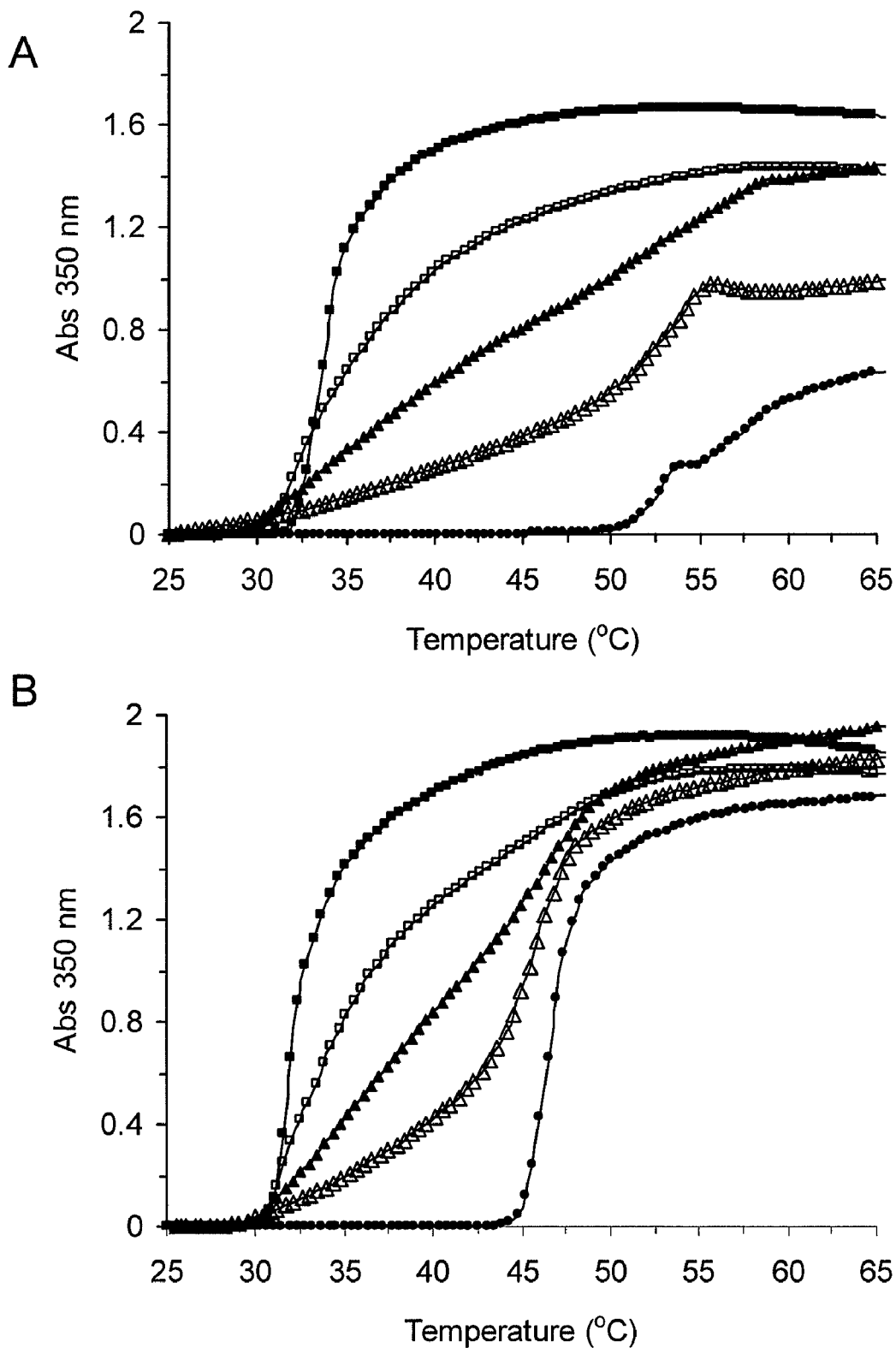
FIG. 5A-B

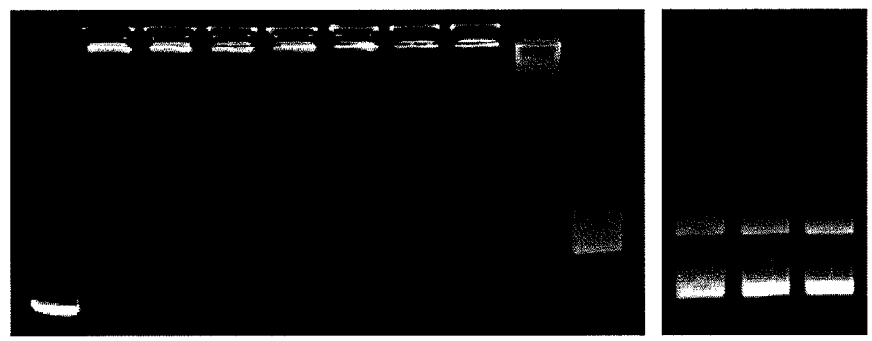
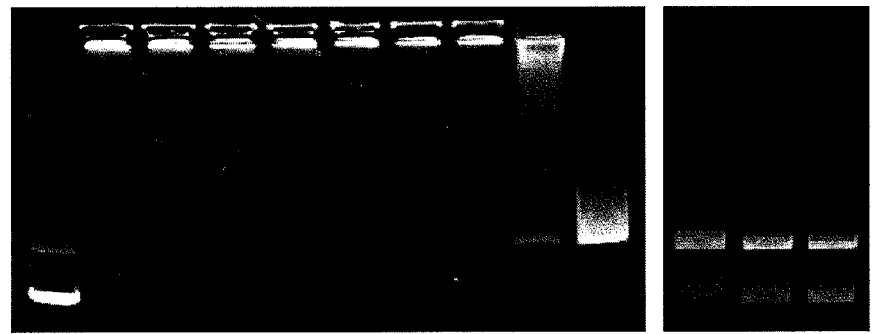
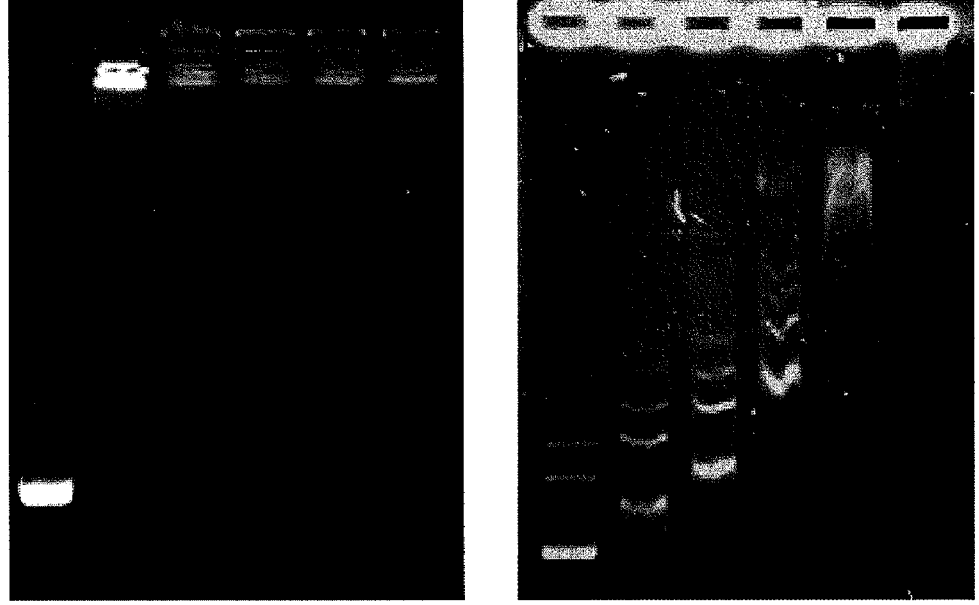
FIG. 7A-C

ELASTIN-LIKE POLYMER DELIVERY VEHICLES

This application claims priority to U.S. provisional patent application Ser. No. 60/799,798 filed May 12, 2006 and U.S. provisional patent application Ser. No. 60/832,455 file Jul. 21, 2006, each incorporated by reference in their entirety.

BACKGROUND OF THE INVENTION

I. Field of the Invention

The invention generally concerns the fields of medicine and molecular biology. In particular, the invention concerns polypeptides for delivery of therapeutic molecules method for the use thereof.

II. Description of Related Art

In the past, therapeutic compositions have generally been delivered by passive or nonspecific targeting. Passive targeting includes targeting based upon size, ionic state, and biological factors and is limited the ability of the therapeutic to diffuse to its site action and the rate of clearance for the therapeutic. Intravenously injected molecules, for example, may have to traverse a cell membrane to reach a site of action and may be readily processed or degraded by the body, thus limiting the use of many therapeutics. To address this issue, synthetic polymers such as poly(N-isopropylacrylamide) (Schild, 1992), poly(ethylene glycol)-block-poly(caprolactone) copolymers (Kim et al., 2004), poly(ethylene oxide)-poly(propylene oxide) multiblock copolymers (Sosnik and Cohn, 2005), and multiple hydrogen bonding-poly(butylenes terephthalate) (Yamauchi et al., 2004) have been used as monolithic gels to deliver drugs. Unfortunately, synthetic polymers such as these suffer from the effects of polydispersity, lack of architectural control, variable levels of biocompatibility, and complex synthesis schemes.

Thus, on merely a biophysical basis, genetically engineered biopolymers such as elastin-like polymers (ELP) pose an attractive alternative to traditional polymer macromolecules for gene and drug delivery due to their monodispersity, non-immunogenicity, and unparalleled control of architecture and biophysical characteristics ("smart" polymer behaviors, ionization state, hydrophobicity). Genetic engineering confers precise control of the biophysical characteristics of biopolymers, a level of control yet to be realized in synthetic polymer syntheses. Through molecular biology techniques, the pentapeptide sequence, molecular weight, and architecture of the ELP can be precisely controlled for subsequent an purified as a recombinant polypeptide, resulting in monodisperse, non-immunogenic (Urry et al., 1991) ELP biopolymers with variable ionic and hydrophobicity characteristics. Traditional synthetic polymers lack this degree of molecular weight control and viral gene carriers suffer from intrinsic immunogenicity; therefore, there is significant promise for the use of genetically engineered polymers in gene and drug delivery (Kopecek, 2003).

Genetically engineered biopolymers show great promise as macromolecule, gene and drug carriers due to genetic control of composition and monodispersity. Moreover, elastin-like polymers are thermosensitive enabling methods for hyperthermic targeting to specific sites for therapy. The use of ELP-biomacromolecules-ELP biopolymers for the delivery of drugs (Dreher et al., 2003; Herrero-Vanrell et al., 2005) and peptides (Bidwell and Raucher, 2005) has been reported. However, previously there has not been a effective ELP platform that could be used to deliver the array of therapies currently in use in the medical field.

SUMMARY OF THE INVENTION

The instant invention overcomes deficiencies in the prior art by providing a polypeptide delivery vehicle for therapeutic compositions. Polypeptide delivery vehicles of the invention generally comprise an elastin-like polypeptide (ELP) in complex with a therapeutic molecule. For example, such an ELP composition may comprise an ELP complexed with a therapeutic small molecule, polypeptide or nucleic acid. In some cases, an ELP may be covalently linked to a therapeutic molecule. For instance, an ELP composition may comprise an ELP domain covalently linked to a small molecule or an ELP linked to a therapeutic polypeptide by a peptide bond (i.e. an ELP fusion protein). In some further cases an ELP may be fused with a polypeptide that binds to a therapeutic molecule.

As used herein the terms "elastin-like polypeptide" or "elastin-like polymer" (ELP) are used interchangeably. ELP refers to a class of amino acid polymers that undergo a conformation change dependent upon temperature. By increasing the temperature ELPs transition from elongated chains that are highly soluble into tightly folded aggregates with greatly reduced solubility (see U.S. Pat. No. 6,852,834). An ELP may, for example, be defined by the median temperature at which this phase transition occur. Thus, in certain aspects of the invention, an ELP will have a median phase transition temperature above about 37° C. In some further embodiments, an ELP may have a median phase transition temperature in a physiological range such as a transition temperature of about 38° C., 39° C., 40° C., 41° C., 42° C., 43° C., 44° C., 45° C. or 46° C. In some cases, ELPs may also be defined based upon the temperature range over which the phase transition occurs. For example, in some cases, the phase transition will occur over a temperature range of less than about 5° C. For instance phase transition may occur in a temperature range of about 4° C., 3° C., 2° C., 1° C. or less.

In some more specific embodiments of the invention, an ELP domain may be defined by its amino acid sequence. For example, an ELP domain may comprise multiple repeats of the amino acid sequence VPGXG (SEQ ID NO:1), wherein X is any amino acid except proline. For example, an ELP of the invention may comprise 10 to 500 repeats of the VPGXG sequence. In some even more specific cases, an ELP of the invention may comprise between 50 and 300 or 80 and 200 amino acids. In some embodiments, the "X" residues in an ELP will all be the same amino acid, however certain other cases an ELP may comprise a variety different residues in the X position throughout the polymer. For example, in some cases X may be an alanine, a valine or a glycine residue, such as an ELP that comprises 10 VPGXG repeats wherein X=Val for the first five repeats, X=Ala for the next two repeats and X=Gly for the remaining 3 repeats (denoted $V_5:A_2:G_3$). As discussed further below, the sequence of an ELP may be further modified by amino acid substitutions deletion or insertions. Such changes in the ELP amino acid sequence may be used, for example, in order to adjust the median phase transition temperature or the range at which phase transition occurs.

In further embodiments of the invention, an ELP composition comprises an ELP and a nucleic acid binding moiety. In certain cases, the nucleic acid binding moiety may be conjugated to the ELP, for example via a covalent chemical conjugation. However, in some other cases, the nucleic acid binding moiety is a polypeptide and the ELP composition may be a fusion protein comprising an ELP domain and the nucleic acid binding domain. Any nucleic acid binding polypeptide know in the art may be used for an ELP composition of the invention. For example, a nucleic acid binding domain may bind to a specific nucleic acid sequence, such as the RNA binding domains of iron regulatory protein (IRP) 1 or 2. In certain additional cases, the nucleic acid binding sequence may bind to nucleic acids non-specifically, such as amino acid polymers that are rich in cationic residues. For example, a nucleic acid binding domain may have of 25%, 30%, 35%, 40%, 45%, 50% or more residues that are positively charged at physiological pH, such as lysine. In certain instances, a nucleic acid binding protein may comprise repeats of the amino acid sequence VK or VKG. For instance, the sequence may have 4 to 100 VK or VKG repeats or a mixture thereof, such as nucleic acid binding domain with 4, 8, 12, 16, 20, 24, 28, 32, 36, 40, 44, 48, 52, 56, 60, 64, 68, 72, 76, 80, 84, 88, 92, 96 or 100 VK or VKG repeats.

In yet further embodiments of the invention, an ELP composition may comprise a cell targeting domain. Such a domain may be conjugated to an ELP composition of the invention. In certain cases, an ELP composition may be a fusion protein comprising an ELP domain and a cell targeting domain, and it yet further cases such a fusion protein may also comprise a nucleic acid binding domain. A cell targeting domain may, for example, be an antibody, a ligand, a cytokine or a chemokine. Cell targeting antibodies include, but are not limited to, polyclonal antibodies, monoclonal antibodies, single chain antibodies, antibody fragments, or humanized antibodies. In another example, a cell targeting ligand may be VEGF or the amino acids there from that mediate receptor binding. Cell targeting domains may preferentially bind to certain classes of cells such as immune cells, cancer cells, or cells from a particular tissue or lineage. In certain aspects of the invention, cell targeting moieties may also mediate internalization an ELP composition.

In still further embodiments of the invention, an ELP composition may comprise a membrane translocation or cell localization domain. Such a domain may be conjugated to an ELP composition of the invention. Furthermore, an ELP composition may be a fusion protein comprising an ELP domain and membrane translocation domain or cell localization domain. Such a fusion protein, in some cases, may also comprise a nucleic acid binding domain. For example, an ELP composition may comprise a membrane translocation domain such as amino acids for the HIV tat protein or the drosophila antennapedia protein. In some additional aspects, an ELP composition comprises a cell localization domain, such as a nuclear localization signal, a secretion signal, an endoplasmic reticulum retention signal, a lysosome localization signal or a mitochondrial localization signal.

In yet further embodiments of the invention, an ELP composition may comprise an ELP domain and a small molecule drug. In this case the ELP compositions may be complexed with or conjugated to the small molecule. For example, a drug may be chemically conjugated to the ELP domain or conjugated to an additional domain in an ELP composition. In some further embodiments, an ELP composition may comprise a polypeptide domain that specifically binds to a small molecule. For example, an ELP composition may be conjugated to cisplatin, or doxorubicin. ELP compositions comprising small molecules may comprise additional domains such as a nucleic acid binding domain or therapeutic polypeptide domain.

In still further embodiments of the invention, there is provided an ELP composition comprising an ELP domain and a therapeutic polypeptide domain. In certain aspects of the invention, a therapeutic polypeptide domain may be chemically conjugated to an ELP domain, however in certain cases the ELP and therapeutic polypeptide domains may be comprised in a fusion protein. Therapeutic polypeptides for use the instant invention include, but are not limited to, cytokines, chemokines, angiogenic factors, anti-angiogenic factors. In some specific examples, a therapeutic polypeptide may be interferon (IFN)-α, IFN-β, IFN-γ, IFN-τ, tumor necrosis factor (TNF)-α, HIF-1α, vascular endothelial growth factor (VEGF), fibroblast growth factor (FGF), platelet derived growth factor (PDGF), NF-κB inhibiting sequences, consensus interferon sequences, interleukin (IL)-2, IL-12, IL-4, IL-8 or a single chain antibody sequence (scFv) such as a VEGF specific scFv. In certain aspects of the invention, a therapeutic polypeptide may comprise an extra cellular domain of a receptor protein, such as VEGF receptor (VEGFR)-1 (Flt-1), VEGFR-2 (Flk-1/KDR) or VEGFR-3.

In some additional embodiments, an ELP composition may comprise a spacer or linker domain. A spacer domain may, for example, be positions between any two domains in an ELP composition fusion protein. A spacer domain of the invention can comprise any number of amino acids and may include a variety of amino acid residues. For instance, a spacer region may comprise 3 or more histidine residues. Such a polyhistidine region can act as a pH buffer in an ELP composition. In some additional cases, spacer regions may comprise amino acids that are sensitive to proteinase cleavage, for example, proteinase cleavage induced by heat, cell stress or pH (e.g. low pH). In certain very specific cases, a proteinase sensitive sequence may be sensitive to an intracellular proteinase, an extracellular proteinase or a proteinase that is associated with metastasis of cancers such as matrix metalloproteinase (MMP).

It will be understood by one of skill in the art that domains of an ELP composition may be positioned in a variety orientations relative to one another. For example, in the case where an ELP composition is a fusion protein the ELP domain may be positioned near the amino terminus, near the carboxyl terminus or in the middle of the fusion protein. In certain aspects of the invention a an ELP composition fusion protein may comprise, from amino terminus to carboxyl terminus, a DNA binding domain, optionally a spacer domain, an ELP domain, optionally a linker domain and optionally a cell targeting domain or a membrane translocation domain.

In some embodiments, an ELP delivery is a fusion protein. Thus, there is provided a nucleic acid that encodes an ELP composition. Such a nucleic acid comprising the coding sequence for an ELP composition may also include addition sequences. For, example sequence for prokaryotic or eukaryotic expression of an ELP composition may be provided. Thus, included as part of the invention is a method for making an ELP composition, for example by expressing a nucleic acid encode the ELP composition in cell, such as bacterial cell. It will also be understood that the thermal transition properties of the ELP domain may be employed to aid in the purification of such ELP compositions (see for example, U.S. Pat. No. 6,852,834).

In some further aspects of the invention, there is provided an ELP composition comprising an ELP domain and a nucleic acid binding domain complexed with a nucleic acid. The complex of an ELP composition and a nucleic acid is herein termed a "bioplex." For example, a bioplex of the invention may comprise an ELP composition, such as a fusion protein comprising an ELP domain and a nucleic acid binding domain complexed with a therapeutic nucleic acid. A bioplex of the invention may comprise a DNA or RNA molecule. For example, nucleic acids that may be used in a bioplex of the invention include, but are not limited to, DNA expression vectors, RNA expression vectors, siRNAs, miRNAs and ribozymes. Bioplex nucleic acids may in some cases be therapeutic nucleic acids that may be used in gene therapy. For example, a therapeutic nucleic acid may induce apoptosis in cancer cells or restore the function a mutant gene to correct a genetic disorder.

In some aspects of the invention, a bioplex may be further defined by its temperature transition characteristics. A bioplex may, for example, be defined by the temperature at which phase transition (mediated by the ELP domain) occurs. Thus, in certain aspects of the invention, a bioplex will have a median phase transition temperature above about 37° C. In some further embodiments, a bioplex may have a median phase transition temperature in a physiological range such as a transition temperature of about 38° C., 39° C., 40° C., 41° C., 42° C., 43° C., 44° C., 45° C. or 46° C. In some further cases, bioplexes of the invention may also be defined based upon the temperature range over which the phase transition occurs, for example in some cases the phase transition will occur over a temperature range of less than about 5° C. For instance, phase transition may occur in a temperature range of about 4° C., 3° C., 2° C., 1° C. or less. It will be understood by the skilled artisan that in some aspects of the invention a bioplex that comprises bound nucleic acid will release at least 20, 30 40, 50, 60, 70, 80, 90, 95 percent or more of the bound nucleic acid at temperatures above the transition temperature for the bioplex.

In still other aspects of the invention, a bioplex may be defined by the median diameter of the bioplex. For instance, a bioplex may have a median diameter of less than about 1 μm. In yet more specific instances, a bioplex of the invention may be defined having a median diameter of about or less than about 500, 400, 300, 200, 100 or 50 nM. Thus, in certain cases, a plurality of bioplexes may be defined by the average median diameter within the plurality of bioplexes (e.g. the plurality of bioplexes may have an average median diameter of less than about 1 μm).

In yet further aspects of the invention, a bioplex may be defined by the ratio of ELP composition to nucleic acid in the bioplex. In some aspects, the ELP composition to nucleic acid ratio may be defined as a simple molar ratio. However, in further cases, a ratio may be defined as the ratio of the amino acid nitrogens (in a nucleic acid binding domain) to nucleic acid phosphates (N/P). Thus, in certain aspects of the invention, the N/P ration may be between about 50 to 1 (50/1) and about 1 to 1 (1/1). In still further aspects, a bioplex may have an N/P ration of about 50/1, 45/1, 40/1, 35/1, 30/1, 25/1, 20/1, 15/1, 10/1, 9/1, 8/1, 7/1, 6/1, 5/1, 4/1, 3/1, 2/1 or 1/1 or any range derivable therein.

In still further embodiments, there is provided a method for making a bioplex comprising mixing an ELP composition with a nucleic acid molecule. Furthermore, there is provided a method for delivery of a therapeutic nucleic acid to a cell comprising, mixing the therapeutic nucleic acid with an ELP composition (comprising an ELP and a nucleotide binding sequence) to form a bioplex and contacting the cell with the bioplex. In certain aspects, the ELP composition may be further defined as a fusion protein comprising at least ELP domain and a nucleic acid binding domain. In some cases, it will be understood that the soluble bioplex may be used to transfect cells with a nucleic acid. However, in certain aspects of the invention, a bioplex may be transitioned into an insoluble form in order to transfect a cell. A bioplex may be transitioned into an insoluble form (i.e., an aggregate) either before or after contacting a cell with the bioplex. In some specific cases, a bioplex maybe transitioned into an insoluble form by the application of heat (i.e., by increasing the temperature of the bioplex).

Certain aspects of the invention concern methods for delivery of a nucleic acid to a cell by contacting the cell with a bioplex. It will be understood that such methods may comprise in vitro, ex vivo or in vivo nucleic acid delivery. Thus, in some cases a bioplex may be used to deliver a nucleic acid to a cell that is in an animal, such as a human. In these cases the bioplex may be administered by a variety of routes including, but not limited to, administering the bioplex intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, locally, by inhalation (e.g., aerosol inhalation), by injection, by infusion or by continuous infusion.

In yet further embodiments of the invention, it will be understood that a bioplex may be administered to an animal in combination with other therapies. In particular, administration of a bioplex may be used in combination with hyperthermia (heat therapy). Hyperthermia may be applied before, after or essentially simultaneously with the administration of a bioplex. In some aspects of the invention, hyperthermia may be applied to the whole body of an animal. However, in some other cases, hyperthermia may be applied locally. For example, hyperthermia may be applied only to a specific region of the body such as a wound, an organ, a site of infection or a tumor. It will be understood that hyperthermia therapy may comprise increasing the temperature of a region to any temperature that is above that of a normal, healthy, animal. For example, in the case of a human hyperthermia therapies may comprise raising the temperature of region to above about 37° C. Furthermore, the temperature of a region may be raised to between about 38° C. and about 46° C. In some very specific cases, the temperature may be raised to about or at least about 38° C., 39° C., 40° C., 41° C., 42° C., 43° C., 44° C., or 45° C.

Thus, in certain specific aspects, a hyperthermia temperature may be raised to a temperature that is above the transition temperature a bioplex. For instance, following administration of a bioplex hyperthermia may be applied to one or more locations wherein the temperature at the application site is about 0.5° C., 1.0° C., 1.5° C., 2.0° C., 2.5° C. or greater than the transition temperature of a bioplex thereby enabling maximal bioplex aggregation at the site(s). Furthermore, hyperthermia may be applied in two or more cycles thereby allowing bioplex aggregation over an extend time period. In still further aspects of the invention, hyperthermia may be applied to one or more sites wherein the temperature at the application site reaches a temperate about 1.5° C., 1.0° C., 0.5° C. or less above or below the transition temperature of a bioplex thereby allowing enabling slow bioplex aggregation and/or accumulation at the site. Thus, in certain aspects the invention provides a method for dosed delivery of bioplex to a site of hyperthermia.

In still further aspects, there is provided a method for delivery of a nucleic acid to an animal comprising obtaining a nucleic acid bound to a bioplex, administering the nucleic acid bioplex to the animal and administering a hyperthermic therapy to the animal thereby releasing the bound nucleic acid from the bioplex. In some aspects, a nucleic acid bound to a bioplex may be administered systemically or locally. In either case nucleic acid release may be controlled by whole body or localized hyperthermic therapy. Thus, in some embodiments the invention provides methods for localized nucleic acid release in an animal. It is contemplated that hyperethermia may, in certain cases, be applied to more than one location on/in the animal or may be applied multiple times. For instance following administration of a bioplex comprising nucleic acid hyperthermia may be applied in two or more cycles (i.e., cycles of hot and cold) thereby allowing release of bound nucleic acid over an extend time period. In still further aspects, hyperthermia may be applied such that the site of application reaches a temperate about 1.5° C., 1.0° C., 0.5° C. or less above or below the transition temperature of the bioplex thereby enabling a slow release of bound nucleic acid over an extended time period. Alternatively, hyperthermia may be applied to one or more sites where in the temperature at the application site is about 0.5° C., 1.0° C., 1.5° C., 2.0° C., 2.5° C. or greater above the transition temperature of a bioplex thereby enabling the release of a maximal amount of the nucleic acid.

Furthermore, in certain aspects of the invention, there is provided a method for treating a disease in an animal comprising mixing a therapeutic nucleic acid with an ELP composition (comprising an ELP domain and a nucleotide binding domain) to form a bioplex and administering an effective amount of the bioplex to the animal. Such a method may be used in accordance with any of the ELP composition or bioplex embodiments described herein. It will further be understood that methods of treating a disease with bioplex compositions may be used in combination or in conjunction with additional therapies such as hyperthermia, chemotherapy, surgical therapy, radiotherapy, immunotherapy, or additional types of gene therapy. It will also be understood that methods and compositions of the invention may be adapted to treat a variety of diseases including but not limited to a wound, a cardiovascular disease, an infection, a genetic disorder, an autoimmune disease or a cell proliferative disease such as cancer. For example, in some specific cases methods of the invention concern the treatment of a cancer such as a melanoma, non-small cell lung, small-cell lung, lung, hepatocarcinoma, retinoblastoma, astrocytoma, glioblastoma, gum, tongue, leukemia, neuroblastoma, head, neck, breast, pancreatic, prostate, renal, bone, testicular, ovarian, mesothelioma, cervical, gastrointestinal, lymphoma, brain, colon, sarcoma or bladder cancer. Thus, in some very specific embodiments, there are provided methods for treating tumors with bioplex compositions.

Embodiments discussed in the context of a methods and/or composition of the invention may be employed with respect to any other method or composition described in this application. Thus, an embodiment pertaining to one method or composition may be applied to other methods and compositions of the invention as well.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings are part of the present specification and are included to further demonstrate certain aspects of the present invention. The invention may be better understood by reference to the drawings in combination with the detailed description of specific embodiments presented herein.

FIG. 4A-B: Thermal transition profiles for $(VKG)_8ELP1$-120/pDNA (FIG. 4A) and $(VKG)_8ELP$ 1-180/pDNA (FIG. 4B) bioplexes. In each case the N/P ratio is indicated on the left.

FIG. 5A-B: Thermal transition profiles for 6.25 µM micelle solutions of $(VKG)_{16}ELP1$-120/DNA (FIG. 5A) and $(VKG)_{16}ELP1$-180/DNA (FIG. 5B). The micelle solutions are prepared by mixing (VKG)4aELP (closed circles) with DNA at N/P ratio 1 (closed squares), 2.5 (open squares), 5 (closed triangles), and 10 (open triangles).

FIG. 7A-C: Release of DNA from ELP/pDNA bioplexes. At physiological pH by using poly(aspartic acid) (FIG. 5A-B) or hyperthermia (FIG. 5C). The Aspartate/Phosphate ratio is indicated at the top of each figure. A, pDNA release from $(VKG)_8ELP1$-120/pDNA complexes. B, pDNA release from $(VKG)_8ELP1$-180/pDNA. C, A hyperthermic DNA releaseassay with ELP/DNA ($(VKG)_8ELP$ 1-120/pDNA) micelles run at 25° C. (left panel) or at 43.5° C. (right panel). Complexation and electrophoretic conditions are otherwise identical. Samples are complexed for ~12 hr and run on a 0.8% agarose gel for 45 min at 150 V. Gels are post-stained in an EtBr solution.

DETAILED DESCRIPTION OF THE INVENTION

Figure 1:
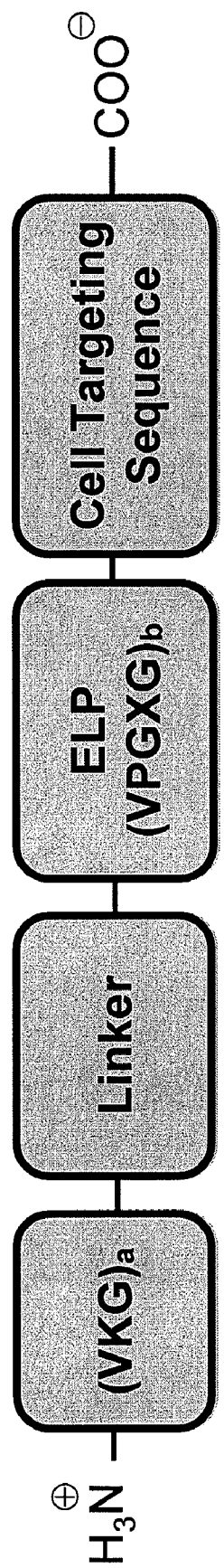
FIG. 1: Schematic of the proposed cationic ELP gene delivery system containing (i) DNA-binding domain, (ii) pH-buffering domain, (iii) thermosensitive domain, and (iv) endothelial cell targeting domain. Specific Aim #2 adds the pH-buffering domain and Specific #3 the endothelial cell-targeting RGD peptide.

Successful in vivo delivery of therapeutic compositions involves a number obstacles. For example, in vivo therapeutics must have a long enough stability to be effective, be soluble at effective concentrations and be able reach the site of action for the therapy. In vivo delivery of gene therapy agents, for example, has proven problematic in that nucleic acids must be stabilized to prevent degradation and further must reach therapeutically effective concentrations at their site of action. Previously, these problem have been addressed by providing viral vectors or by encasing the nucleic acids in liposomes or synthetic polymers. However, none of these techniques is optimal since viral vectors can be target by a patients immune system and can only deliver therapy to cells that comprise the viral receptor. On the other hand, liposomal compositions do not enable therapeutic nucleic acids to be delivered in a targeted manner. Thus, previously, there have not been completely effective therapeutic delivery vehicles that can specifically target molecules, like nucleic acids to a site of action.

The studies herein demonstrate that elastin-like biopolymers (polypeptide) can be used as effective gene therapy delivery vehicles. Experimental results here show that ELP domains can be fused with a nucleic acid binding domain and that these compositions can be form stable complexes with nucleic acids (Example 3). Interestingly, these bioplexes, to a large extent, maintain the thermal transition properties of an ELP in that the complexes can be induced to aggregate by increasing the temperature of a solution (see FIGS. 2-4). Importantly, when applied to cells the bioplexes can deliver a nucleic acid into a cell resulting in expression of an encoded gene (FIG. 5). These studies clearly indicate that ELP delivery vehicles may be used deliver therapeutic molecules, such as nucleic acids to cells thus, enabling new methods for administration of therapeutic molecules.

Thus, invention sets forth a unique approach to in vivo therapeutic delivery by providing a biopolymer delivery composition. The composition is highly soluble in aqueous solutions, but can be caused to aggregate along with its therapeutic payload, by increasing the local temperature. Thus, delivery vehicles described herein may be introduced systemically in a patient. In cases where a local therapeutic is preferable, the temperature in a localized region may be raised. This temperature increase induces aggregation of the delivery composition thereby concentrating therapeutic molecules at the target sites. These new therapeutic methods and compositions may be useful for increasing the effectiveness of a variety of therapies, such as gene therapies. Additionally, localized delivery of therapeutics may reduce the side effects associates with currently available treatments.

I. NUCLEIC ACIDS

The present invention concerns a number of different types of nucleic acid molecules that can be used in a variety of ways. In some embodiments of the invention, the nucleic acid is a recombinant nucleic acid. The term "recombinant" is used according to its ordinary and plain meaning to refer to the product of recombinant DNA technology, e.g., genetically engineered DNA prepared in vitro by cutting up DNA molecules and splicing together specific DNA fragments, which may or may not be from different organisms. Things that have or are from a genetically engineered DNA are similarly recombinant; this includes replicated or duplicated products based on the initially engineered DNA. In particular embodiments, the invention concerns therapeutic nucleic acids recombinant DNA and RNA molecules.

In some embodiments, the nucleic acid molecule is a DNA molecule, for example, a DNA molecule whose expression gives rise to the RNA transcript. Alternatively, the DNA molecule may be used in a protein expression expression (e.g., ELP compositions) or a therapeutic method of the invention or the molecule may encode an RNA transcript or polypeptide that is used in such methods. These different DNA molecules may or may not be in an expression construct such as a vector or in a host cell. Further details are provided below.

The present invention concerns polynucleotides, isolatable from cells, that are free from total genomic DNA and that are capable of expressing all or part of an RNA molecule, RNA transcript, protein or polypeptide. The polynucleotide may be an RNA molecule such as an siRNA, an miRNA or a ribozyme. Alternatively, a polynucleotide may encode a peptide or polypeptide having all or part of the amino acid sequence of a therapeutic protein.

Embodiments of the invention concern isolated and/or recombinant polynucleotides. An isolated polynucleotide refers to a polynucleotide that is separated from a cell and its non-nucleic acid contents, and more specifically, may be separated from other nucleic acid sequences. A recombinant polynucleotide refers to a genetically engineered nucleic acid molecule or products of such a molecule (either through duplication, replication, or expression).

As used in this application, the term "transcript" refers to a ribonucleic acid molecule (RNA) that in some embodiments of the invention is generated from a recombinant DNA molecule. In particular embodiments, polynucleotides of the invention concern transcripts that encode ELP compositions or that may be used as a gene therapy therapeutic.

The term "cDNA" is intended to refer to DNA prepared using messenger RNA (mRNA) as template. In many embodiments of the invention, the nucleic acid is a cDNA or cDNA sequence. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

It also is contemplated that a particular RNA molecule or transcript from a given species may be represented by natural variants that have slightly different nucleic acid sequences but, nonetheless, encode what is considered a wild-type sequence.

It is contemplated that nucleic acid molecules encoding RNA molecules with a nucleotide repeat region may be used in method and compositions of the invention. Furthermore, candidate substances or compounds, candidate therapeutic agents, or other agents may be employed as nucleic acids, including recombinant nucleic acids in compositions and methods of the invention.

In other embodiments, the invention concerns isolated nucleic acid molecules and recombinant vectors incorporating DNA sequences that encode a polypeptide or peptide that includes within its amino acid sequence a contiguous amino acid sequence in accordance with, or essentially corresponding to the polypeptide.

The nucleic acid segments used in the present invention, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

It is contemplated that the nucleic acid constructs of the present invention may encode part or all (full-length) of transcripts or polypeptides from any source. Alternatively, a nucleic acid sequence may encode an RNA or polypeptide with additional heterologous sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a sequence that is not the same from the same source as other sequences.

In certain other embodiments, the invention concerns isolated DNA or RNA segments and recombinant vectors that include within their sequence the coding sequence for an ELP composition or a therapeutic protein. One of skill in the art will understand the due to the degeneracy of the genetic code a variety of nucleic acid sequence can encode a single amino acid sequence (see for instance the codons listed in Table 1). Therefore, it is contemplated that any nucleic acid sequence capable of encoding a polypeptide of the invention is included as part of the instant invention.

TABLE 1

Preferred Human DNA Codons

| Amino Acids | | | Codons | | | | | |
|---|---|---|---|---|---|---|---|---|
| Alanine | Ala | A | GCC | GCT | GCA | GCG | | |
| Cysteine | Cys | C | TGC | TGT | | | | |
| Aspartic acid | Asp | D | GAC | GAT | | | | |
| Glutamic acid | Glu | E | GAG | GAA | | | | |
| Phenylalanine | Phe | F | TTC | TTT | | | | |
| Glycine | Gly | G | GGC | GGG | GGA | GGT | | |
| Histidine | His | H | CAC | CAT | | | | |
| Isoleucine | Ile | I | ATC | ATT | ATA | | | |
| Lysine | Lys | K | AAG | AAA | | | | |
| Leucine | Leu | L | CTG | CTC | TTG | CTT | CTA | TTA |
| Methionine | Met | M | ATG | | | | | |
| Asparagine | Asn | N | AAC | AAT | | | | |
| Proline | Pro | P | CCC | CCT | CCA | CCG | | |
| Glutamine | Gln | Q | CAG | CAA | | | | |
| Arginine | Arg | R | CGC | AGG | CGG | AGA | CGA | CGT |
| Serine | Ser | S | AGC | TCC | TCT | AGT | TCA | TCG |
| Threonine | Thr | T | ACC | ACA | ACT | ACG | | |
| Valine | Val | V | GTG | GTC | GTT | GTA | | |
| Tryptophan | Trp | W | TGG | | | | | |
| Tyrosine | Tyr | Y | TAC | TAT | | | | |

A number of additional embodiments in the context of nucleic acids are discussed below.

A. Vectors

RNA molecules, peptides and polypeptides may be encoded by a nucleic acid molecule comprised in a vector. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al., (1989) and Ausubel et al., 1996, both incorporated herein by reference. A targeting molecule is one that directs the modified polypeptide to a particular organ, tissue, cell, or other location in a subject's body.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of RNA molecules used in methods of the invention. Expression vectors can contain a variety of "control sequences," which refer to nucleic acid sequences necessary for the transcription and possibly translation of an operably linked coding sequence in a particular host organism. For instance, in some embodiments of the invention, there may sequences to allow for in vitro transcription of a sequence. In particular embodiments, the expression vector may contain an Sp6, T3, or T7 promoter. In addition to control sequences that govern transcription and translation, vectors and expression vectors may contain nucleic acid sequences that serve other functions as well and are described infra.

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," e.g., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. No. 4,683,202, U.S. Pat. No. 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it may be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

In certain embodiments of the invention, a vector may also include one or more of: an ATG initiation signal, internal ribosome binding sites, multiple cloning site (MCS), splicing site, termination signal, polyadenylation signal, origin of replication, or selectable or screenable marker (drug resistance marker, enzymatic marker, calorimetric marker, fluorescent marker).

In certain embodiments of the invention, the expression vector comprises a therapeutic gene for example, a vector may comprise the coding sequence for VEGF. This kind of vector may be useful in the treatment for example of myocardial infection. In some other cases a therapeutic expression vector may encode a HIF-1α gene. It is additionally contemplated that an expression vector for use in the current invention may encode an angiogenic factor, an anti-angiogenic factor, an interferon, a cytokine, a chemokine, a tumor suppressor, a protein kinase, a protein phosphotase, a cell surface receptor (or the extra cellular domain thereof), a growth factor or an enzyme.

B. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. Such a host cell would be considered recombinant if the heterologous nucleic acid sequence was the product of recombinant DNA technology. A host cell can, and has been, used as a recipient for vectors. A host cell may be "transfected" or "transformed," which refers to a process by which exogenous nucleic acid, such as a modified protein-encoding sequence, is transferred or introduced into the host cell. A transformed cell includes the primary subject cell and its progeny.

Host cells may be derived from prokaryotes such as bacteria or eukaryotes, including yeast cells, insect cells, and mammalian cells, depending upon whether the desired result is replication of the vector or expression of part or all of the vector-encoded nucleic acid sequences. In certain embodiments, the cell is an embryonic stem cell, such as from a mouse.

Numerous cell lines and cultures are available for use as a host cell, and they can be obtained through the American Type Culture Collection (ATCC), which is an organization that serves as an archive for living cultures and genetic materials (World Wide Web at atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include but are not limited to XL-10-Gold and SURE 2 (Stratagene), which have been employed in the Examples. Additional bacterial cells are DH5α, JM109, and KC8, as well as a number of commercially available bacterial hosts such as SURE® Competent Cells and SOLOPACK™ Gold Cells (STRATAGENE®, La Jolla, Calif.). Alternatively, bacterial cells such as *E. coli* LE392 could be used as host cells for phage viruses. Appropriate yeast cells include *Saccharomyces cerevisiae, Saccharomyces pombe*, and *Pichia pastoris*.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

C. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. For example, high yield expression in sect cells such as SF-9 cells, may be accomplished by baculoviral expression systems. Another useful eukaryotic expression system is yeast which can be used to produce relatively large amounts of protein at a low cost. Many such systems are commercially and widely available.

D. Antisense Molecules, Ribozymes, and siRNA

In some embodiments of the invention, therapeutic nucleic acids are nucleic acid molecules with complementarity to target molecules. Such nucleic acids include antisense molecules, ribozymes, and siRNAs that are targeted to particular sequences based on the desired goal. In certain embodiments, for instance, a Notch may be inhibited or inactivated using an siRNA that targets a component of the Notch activation pathway, such as γ-secretase. Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNAs, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs may include regions complementary to intron/exon splice junctions. Thus, antisense constructs with complementarity to regions within 50-200 bases of an intron-exon splice junction may be used. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g. ribozyme) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

The use of ribozymes is claimed in the present application. The following information is provided in order to compliment the earlier section and to assist those of skill in the art in this endeavor.

Ribozymes are RNA-protein complexes that cleave nucleic acids in a site-specific fashion. Ribozymes have specific catalytic domains that possess endonuclease activity (Kim and Cech, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence specific cleavage/ligation reactions involving nucleic acids (Joyce, 1989; Cech et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990; Sioud et al., 1992). Recently, it was reported that ribozymes elicited genetic changes in some cell lines to which they were applied; the altered genes included the oncogenes H-ras, c-fos and genes of HIV. Most of this work involved the modification of a target mRNA, based on a specific mutant codon that is cleaved by a specific ribozyme. In light of the information included herein and the knowledge of one of ordinary skill in the art, the preparation and use of additional ribozymes that are specifically targeted to a given gene will now be straightforward.

Several different ribozyme motifs have been described with RNA cleavage activity (reviewed in Symons, 1992). Examples that would be expected to function equivalently for the down regulation of AR include sequences from the Group I self splicing introns including tobacco ringspot virus (Prody et al., 1986), avocado sunblotch viroid (Palukaitis et al., 1979 and Symons, 1981), and Lucerne transient streak virus (Forster and Symons, 1987). Sequences from these and related viruses are referred to as hammerhead ribozymes based on a predicted folded secondary structure.

Other suitable ribozymes include sequences from RNase P with RNA cleavage activity (Yuan et al., 1992, Yuan and Altman, 1994), hairpin ribozyme structures (Berzal-Herranz et al., 1992; Chowrira et al., 1993) and hepatitis δ virus based ribozymes (Perrotta and Been, 1992). The general design and optimization of ribozyme directed RNA cleavage activity has been discussed in detail (Haseloff and Gerlach, 1988, Symons, 1992, Chowrira, et al., 1994, and Thompson, et al., 1995).

The other variable on ribozyme design is the selection of a cleavage site on a given target RNA. Ribozymes are targeted to a given sequence by virtue of annealing to a site by complimentary base pair interactions. Two stretches of homology are required for this targeting. These stretches of homologous sequences flank the catalytic ribozyme structure defined above. Each stretch of homologous sequence can vary in length from 7 to 15 nucleotides. The only requirement for defining the homologous sequences is that, on the target RNA, they are separated by a specific sequence which is the cleavage site. For hammerhead ribozymes, the cleavage site is a dinucleotide sequence on the target RNA, uracil (U) followed by either an adenine, cytosine or uracil (Perriman et al., 1992; Thompson et al., 1995). The frequency of this dinucleotide occurring in any given RNA is statistically 3 out of 16. Therefore, for a given target messenger RNA of 1000 bases, 187 dinucleotide cleavage sites are statistically possible.

Designing and testing ribozymes for efficient cleavage of a target RNA is a process well known to those skilled in the art. Examples of scientific methods for designing and testing ribozymes are described by Chowrira et al., (1994) and Lieber and Strauss (1995), each incorporated by reference. The identification of operative and preferred sequences for use in targeted ribozymes is simply a matter of preparing and testing a given sequence, and is a routinely practiced "screening" method known to those of skill in the art.

An RNA molecule capable of mediating RNA interference in a cell is referred to as "siRNA." Elbashir et al. (2001) discovered a clever method to bypass the anti viral response and induce gene specific silencing in mammalian cells. Several 21-nucleotide dsRNAs with 2 nucleotide 3' overhangs were transfected into mammalian cells without inducing the antiviral response. The small dsRNA molecules (also referred to as "siRNA") were capable of inducing the specific suppression of target genes.

In the context of the present invention, siRNA directed against angiogenic factors, heat shock factors, and oncogene transcripts are specifically contemplated. For example, a siRNA may be directed against VEGF, heat shock protein 70 (HSP70), HSP90, ubiquitin or MMP. The siRNA can target a particular sequence because of a region of complementarity between the siRNA and the RNA transcript encoding the polypeptide whose expression will be decreased, inhibited, or eliminated.

An siRNA may be a double-stranded compound comprising two separate, but complementary strands of RNA or it may be a single RNA strand that has a region that self-hybridizes such that there is a double-stranded intramolecular region of 7 basepairs or longer (see Sui et al., 2002 and Brummelkamp et al., 2002 in which a single strand with a hairpin loop is used as a dsRNA for RNAi). In some cases, a double-stranded RNA molecule may be processed in the cell into different and separate siRNA molecules.

In some embodiments, the strand or strands of dsRNA are 100 bases (or basepairs) or less, in which case they may also be referred to as "siRNA." In specific embodiments the strand or strands of the dsRNA are less than 70 bases in length. With respect to those embodiments, the dsRNA strand or strands may be from 5-70, 10-65, 20-60, 30-55, 40-50 bases or basepairs in length. A dsRNA that has a complementarity region equal to or less than 30 basepairs (such as a single stranded hairpin RNA in which the stem or complementary portion is less than or equal to 30 basepairs) or one in which the strands are 30 bases or fewer in length is specifically contemplated, as such molecules evade a mammalian's cell antiviral response. Thus, a hairpin dsRNA (one strand) may be 70 or fewer bases in length with a complementary region of 30 basepairs or fewer.

Methods of using siRNA to achieve gene silencing are discussed in WO 03/012052, which is specifically incorporated by reference herein. Designing and testing siRNA for efficient inhibition of expression of a target polypeptide is a process well known to those skilled in the art. Their use has become well known to those of skill in the art. The techniques described in U.S. Patent Publication No. 20030059944 and 20030105051 are incorporated herein by reference. Furthermore, a number of kits are commercially available for generating siRNA molecules to a particular target, which in this case includes AR, NF-κB, and TNF-α. Kits such as Silencer™ Express, Silencer™ siRNA Cocktail, Silencer™ siRNA Construction, MEGAScript® RNAi are readily available from Ambion, Inc.

E. Therapeutic Genes

In certain aspects of the invention, a therapeutic nucleic acid may comprise an RNA or DNA expression vector that can mediate expression of a therapeutic gene. The term "gene" is used for simplicity to refer to a functional protein, polypeptide, or peptide-encoding unit. "Therapeutic gene" is a gene which can be administered to a subject for the purpose of treating or preventing a disease. For example, a therapeutic gene can be a gene administered to a subject for treatment or prevention of cancer. Examples of therapeutic genes include, but are not limited to, Rb, CFTR, p16, p21, p27, p57, p73, C-CAM, APC, CTS-1, zac1, scFV ras, DCC, NF-1, NF-2, WT-1, MEN-I, MEN-II, BRCA1, VHL, MMAC1, FCC, MCC, BRCA2, IL-1, IL-2, IL-3, IL-4, IL-5, IL-6, IL-7, IL-8, IL-9, IL-10, IL-11 IL-12, GM-CSF, G-CSF, thymidine kinase, mda7, fus, interferon α, interferon β, interferon γ, ADP, p53, ABLI, BLC1, BLC6, CBFA1, CBL, CSFIR, ERBA, ERBB, EBRB2, ETS1, ETS2, ETV6, FGR, FOX, FYN, HCR, HRAS, JUN, KRAS, LCK, LYN, MDM2, MLL, MYB, MYC, MYCL1, MYCN, NRAS, PIM1, PML, RET, SRC, TAL1, TCL3, YES, MADH4, RB1, TP53, WT1, TNF, BDNF, CNTF, NGF, IGF, GMF, aFGF, bFGF, NT3, NT5, ApoAI, ApoAIV, ApoE, Rap1A, cytosine deaminase, Fab, ScFv, BRCA2, zac1, ATM, HIC-1, DPC-4, FHIT, PTEN, ING1, NOEY1, NOEY2, OVCA1, MADR2, 53BP2, IRF-1, Rb, zac1, DBCCR-1, rks-3, COX-1, TFPI, PGS, Dp, E2F, ras, myc, neu, raf, erb, fms, trk, ret, gsp, hst, abl, E1A, p300, VEGF, FGF, thrombospondin, BAI-1, GDAIF, or MCC.

Other examples of therapeutic genes include genes encoding enzymes. Examples include, but are not limited to, ACP desaturase, an ACP hydroxylase, an ADP-glucose pyrophorylase, an ATPase, an alcohol dehydrogenase, an amylase, an amyloglucosidase, a catalase, a cellulase, a cyclooxygenase, a decarboxylase, a dextrinase, an esterase, a DNA polymerase, an RNA polymerase, a hyaluron synthase, a galactosidase, a glucanase, a glucose oxidase, a GTPase, a helicase, a hemicellulase, a hyaluronidase, an integrase, an invertase, an isomerase, a kinase, a lactase, a lipase, a lipoxygenase, a lyase, a lysozyme, a pectinesterase, a peroxidase, a phosphatase, a phospholipase, a phosphorylase, a polygalacturonase, a proteinase, a peptidease, a pullanase, a recombinase, a reverse transcriptase, a topoisomerase, a xylanase, a reporter gene, an interleukin, or a cytokine.

Further examples of therapeutic genes include the gene encoding carbamoyl synthetase I, ornithine transcarbamylase, arginosuccinate synthetase, arginosuccinate lyase, arginase, fumarylacetoacetate hydrolase, phenylalanine hydroxylase, alpha-1 antitrypsin, glucose-6-phosphatase, low-density-lipoprotein receptor, porphobilinogen deaminase, factor VIII, factor IX, cystathione beta.-synthase, branched chain ketoacid decarboxylase, albumin, isovaleryl-CoA dehydrogenase, propionyl CoA carboxylase, methyl malonyl CoA mutase, glutaryl CoA dehydrogenase, insulin, beta.-glucosidase, pyruvate carboxylase, hepatic phosphorylase, phosphorylase kinase, glycine decarboxylase, H-protein, T-protein, Menkes disease copper-transporting ATPase, Wilson's disease copper-transporting ATPase, cytosine deaminase, hypoxanthine-guanine phosphoribosyltransferase, galactose-1-phosphate uridyltransferase, phenylalanine hydroxylase, glucocerbrosidase, sphingomyelinase, α-L-iduronidase, glucose-6-phosphate dehydrogenase, HSV thymidine kinase, or human thymidine kinase.

Therapeutic genes also include genes encoding hormones. Examples include, but are not limited to, genes encoding growth hormone, prolactin, placental lactogen, luteinizing hormone, follicle-stimulating hormone, chorionic gonadotropin, thyroid-stimulating hormone, leptin, adrenocorticotropin, angiotensin I, angiotensin II, □-endorphin, β-melanocyte stimulating hormone, cholecystokinin, endothelin I, galanin, gastric inhibitory peptide, glucagon, insulin, lipotropins, neurophysins, somatostatin, calcitonin, calcitonin gene related peptide, β-calcitonin gene related peptide, hypercalcemia of malignancy factor, parathyroid hormone-related protein, parathyroid hormone-related protein, glucagon-like peptide, pancreastatin, pancreatic peptide, peptide YY, PHM, secretin, vasoactive intestinal peptide, oxytocin, vasopressin, vasotocin, enkephalinamide, metorphinamide, alpha melanocyte stimulating hormone, atrial natriuretic factor, amylin, amyloid P component, corticotropin releasing hormone, growth hormone releasing factor, luteinizing hormone-releasing hormone, neuropeptide Y, substance K, substance P, or thyrotropin releasing hormone.

II. PROTEINACEOUS COMPOSITIONS

In certain embodiments, the present invention concerns compositions comprising at least one proteinaceous molecule, such as elastin-like polypeptider. As used herein, a "proteinaceous molecule," "proteinaceous composition," "proteinaceous compound," "proteinaceous chain" or "proteinaceous material" generally refers, but is not limited to, a protein molecule containing at least one polypeptide with multiple amino acids. The protein may contain more than one polypeptide, such as a dimer or trimer or other tertiary structure. In some embodiments, a protein refers to a polypeptide that has 3 amino acids or more or to a peptide of from 3 to 100 amino acids. All the "proteinaceous" terms described above may be used interchangeably herein. In the case of a protein composed of a single polypeptide, the terms "polypeptide" and "protein" are used interchangeably.

In certain embodiments the size of the at least one proteinaceous molecule may comprise, or be at most or at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600 or greater amino molecule residues, and any range derivable therein. Moreover, it may contain such lengths of contiguous amino acids from a polypeptide provided herein, such as an elastin polymer.

As used herein, an "amino molecule" refers to any amino acid, amino acid derivative or amino acid mimic as would be known to one of ordinary skill in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

Accordingly, the term "proteinaceous composition" encompasses amino molecule sequences comprising at least one of the 20 common amino acids in naturally synthesized proteins, or at least one modified or unusual amino acid, including but not limited to those shown on Table 2 below.

TABLE 2

Modified and Unusual Amino Acids

| Abbr. | Amino Acid |
|---|---|
| Aad | 2 Aminoadipic acid |
| Baad | 3 Aminoadipic acid |
| Bala | β alanine, β Amino propionic acid |
| Abu | 2 Aminobutyric acid |
| 4Abu | 4 Aminobutyric acid, piperidinic acid |
| Acp | 6 Aminocaproic acid |
| Ahe | 2 Aminoheptanoic acid |
| Aib | 2 Aminoisobutyric acid |
| Baib | 3 Aminoisobutyric acid |
| Apm | 2 Aminopimelic acid |
| Dbu | 2,4 Diaminobutyric acid |
| Des | Desmosine |
| Dpm | 2,2' Diaminopimelic acid |
| Dpr | 2,3 Diaminopropionic acid |
| EtGly | N Ethylglycine |
| EtAsn | N Ethylasparagine |
| Hyl | Hydroxylysine |
| AHyl | allo Hydroxylysine |
| 3Hyp | 3 Hydroxyproline |
| 4Hyp | 4 Hydroxyproline |
| Ide | Isodesmosine |
| Alle | allo Isoleucine |
| MeGly | N Methylglycine, sarcosine |
| MeIle | N Methylisoleucine |
| MeLys | 6 N Methyllysine |
| MeVal | N Methylvaline |
| Nva | Norvaline |
| Nle | Norleucine |
| Orn | Ornithine |

In certain embodiments the proteinaceous composition comprises at least one protein, polypeptide or peptide. In further embodiments the proteinaceous composition comprises a biocompatible protein, polypeptide or peptide. As used herein, the term "biocompatible" refers to a substance which produces no significant untoward effects when applied to, or administered to, a given organism according to the methods and amounts described herein. Such untoward or undesirable effects are those such as significant toxicity or adverse immunological reactions. In preferred embodiments, biocompatible protein, polypeptide or peptide containing compositions will generally be mammalian proteins or peptides or synthetic proteins or peptides each essentially free from toxins, pathogens and harmful immunogens.

Proteinaceous compositions may be made by any technique known to those of skill in the art, including the expression of proteins, polypeptides or peptides through standard molecular biological techniques, the isolation of proteinaceous compounds from natural sources, or the chemical synthesis of proteinaceous materials. The nucleotide and protein, polypeptide and peptide sequences for various genes have been previously disclosed, and may be found at computerized databases known to those of ordinary skill in the art. One such database is the National Center for Biotechnology Information's Genbank and GenPept databases (on the World Wide Web at ncbi.nlm.nih.gov/). The coding regions for these known genes may be amplified and/or expressed using the techniques disclosed herein or as would be know to those of ordinary skill in the art. Alternatively, various commercial preparations of proteins, polypeptides and peptides are known to those of skill in the art.

In certain embodiments a proteinaceous compound may be purified. Generally, "purified" will refer to a specific or protein, polypeptide, or peptide composition that has been subjected to fractionation to remove various other proteins, polypeptides, or peptides, and which composition substantially retains its activity, as may be assessed, for example, by the protein assays, as would be known to one of ordinary skill in the art for the specific or desired protein, polypeptide or peptide.

In certain embodiments, the proteinaceous composition may comprise at least one antibody, for example, an antibody against a tumor antigen, which may be used to determine whether it is sequestered. As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting.

The term "antibody" is used to refer to any antibody-like molecule that has an antigen binding region, and includes antibody fragments such as Fab', Fab, F(ab')2, single domain antibodies (DABs), Fv, scFv (single chain Fv), and the like. The techniques for preparing and using various antibody based constructs and fragments are well known in the art. Means for preparing and characterizing antibodies are also well known in the art (See, e.g., Harlow et al., 1988; incorporated herein by reference).

It is contemplated that virtually any protein, polypeptide or peptide containing component may be used in the compositions and methods disclosed herein. However, it is preferred that the proteinaceous material is biocompatible. In certain embodiments, it is envisioned that the formation of a more viscous composition will be advantageous in that will allow the composition to be more precisely or easily applied to the tissue and to be maintained in contact with the tissue throughout the procedure. In such cases, the use of a peptide composition, or more preferably, a polypeptide or protein composition, is contemplated. Ranges of viscosity include, but are not limited to, about 40 to about 100 poise. In certain aspects, a viscosity of about 80 to about 100 poise is preferred.

In some further aspects of the invention, it will be understood that the sequence of an ELP domain may be modified, for example, to change the phase transition characteristics of an ELP, ELP composition or bioplex. For instance, in some cases, an ELP domain comprises the sequence VPGXG, wherein X is any amino acid except proline. By substituting of different amino acids at the X position the characteristics of an ELP domain may be modified. For example, in the case where a lower transition temperature is desired more hydrophobic residues may be substituted at X. Conversely, to increase the transition temperature less hydrophobic residues may be substituted at the X position. The importance of hydrophobicity or the hydropathic amino acid index in conferring biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (0.5); histidine −0.5); cysteine (−1.0); methionine (−1.3); valine (−1.5); leucine (−1.8); isoleucine (−1.8); tyrosine (2.3); phenylalanine (−2.5); tryptophan (−3.4). Thus, it will be understood that when the amino acid at position X has a high hydrophilicity value ELP transition temperature can be raised whereas to lower the transition temperature amino acids with lower hydrophilicity values may be used.

It will also be understood that the transition temperature of an ELP domain, ELP composition or bioplex may be modified by changing the number of elastin-like repeats in an ELP domain. For example, in order to raise the transition temperature conferred by an ELP domain the number of ELP repeats may be reduced. Conversely, increasing the number of ELP repeats in an ELP domain will generally decrease the transition temperature of an ELP domain, ELP composition or bioplex.

In additional aspects of the invention polypeptides domains may be further modified by amino substitutions, for example by substituting an amino acid at one or more positions with an amino acid having a similar hydrophilicity (see above). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Thus such conservative substitution can be made in ELP domain, cell targeting domain, a membrane translocation domain, a therapeutic polypeptide domain or a nucleic acid binding domain and such substitutions will likely only have minor effects on their activity. For instance, substitution of amino acids whose hydrophilicity values are within ±2 are preferred, those that are within ±1 are particularly preferred, and those within ±0.5 are even more particularly preferred. Thus, any of the polypeptide domains described herein may be modified by the substitution of an amino acid, for different, but homologous amino acid with a similar hydrophilicity value. Amino acids with hydrophilicities within +/−1.0, or +/−0.5 points are considered homologous.

In certain embodiments, a peptide or polypeptide may contain an amino acid sequence that is identical or similar to a reference sequence or a particular region of the reference sequence. In certain embodiments a peptide or polypeptide has at least or most 60, 65, 70, 75, 80, 85, 90, 95, 96, 97, 98, 99, 99.5, 100% identity with respect to the amino acid sequence of a particular polypeptide or within a region of the particular polypeptide. In some cases, an ELP domain sequence may modified to more closely match the sequence of a human elastin domain, comprising a repeats of the sequence VPGVG. Such modifications may be made, for example, to further reduce the immunogenicity of an ELP domain, ELP composition or bioplex. For instance, in some embodiments of the invention, there an ELP domain may be defined a at least about 60, 65, 70, 75, 80, 85, 90 or 95% identical to the human elastin repeat sequence.

In the case of similar amino acids, certain amino acids can be substituted for one another with minimal effect on protein function. Amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include those in the table below.

TABLE 3

| Original Residue | Exemplary Substitutions |
|---|---|
| Ala | Gly; Ser |
| Arg | Lys |
| Asn | Gln; His |
| Asp | Glu |
| Cys | Ser |
| Gln | Asn |
| Glu | Asp |
| Gly | Ala |
| His | Asn; Gln |
| Ile | Leu; Val |
| Leu | Ile; Val |
| Lys | Arg |
| Met | Met; Leu; Tyr |
| Ser | Thr |
| Thr | Ser |
| Trp | Tyr |
| Tyr | Trp; Phe |
| Val | Ile; Leu |

Accordingly, sequences that have between about 70% and about 80%, between about 81% and about 90%; or between about 91% and about 99%; of amino acids that are identical or functionally equivalent to the amino acids of a reference polypeptide sequence are included as part of the invention.

Another embodiment for the preparation of polypeptides according to the invention is the use of peptide mimetics. Mimetics are peptide-containing molecules that mimic elements of protein secondary structure. See, e.g., Johnson (1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation molecules having many of the natural properties of the original protein, but with altered and even improved characteristics.

A specialized kind of insertional variant is the fusion protein. This molecule generally has all or a substantial portion of the native molecule, linked at the N- or C-terminus, to all or a portion of a second polypeptide. For example, fusions typically employ leader sequences from other species to permit the recombinant expression of a protein in a heterologous host. Another useful fusion includes the addition of an immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes such as a hydrolase, glycosylation domains, cellular targeting signals or transmembrane regions.

In certain aspects of the invention, the charge of an amino acid in a polypeptide is an important characteristic. For example, in the case on an ELP domain charged amino acids can alter the transition temperature conferred by the domain. Another example is a nucleic acid binding domain. In certain aspects, cationic amino acids are use to bind nucleic acids via electrostatic interactions. In these cases, the pH of a solution is important in that it can alter the charge of amino acid and this the characteristics of ELP compositions and bioplexes of the invention (e.g., nucleic acid interaction may be destabilized or ELP transition temperature altered). Table 4 below summarizes the pKa values for the common 20 amino acids an can be used to determine the percentage of any particular amino acid that will charged at a give pH. Of course, it will be understood that in many cases a neutral or physiological pH will be preferred.

TABLE 4

Amino Acid pKa values

| A.A. | Carboxylic acid | Amine | Side Chain |
|---|---|---|---|
| A | 2.3 | 9.9 | — |
| C | 1.8 | 10.8 | 8.6 |
| D | 2.0 | 10.0 | 4.5 |
| E | 2.2 | 9.7 | 4.5 |
| F | 1.8 | 9.1 | — |
| G | 2.4 | 9.8 | — |
| H | 1.8 | 9.2 | 6.8 |
| I | 2.4 | 9.7 | — |
| K | 2.2 | 9.2 | 10.1 |
| L | 2.4 | 9.6 | — |
| M | 2.3 | 9.2 | — |
| N | 2.0 | 8.8 | — |
| P | 2.0 | 10.6 | — |
| Q | 2.2 | 9.1 | — |
| R | 1.8 | 9.0 | 12.5 |
| S | 2.1 | 9.2 | — |
| T | 2.6 | 10.4 | — |
| V | 2.3 | 9.6 | — |
| W | 2.4 | 9.4 | — |
| Y | 2.2 | 9.1 | 9.8 |

A. Protein Purification

In some embodiments, it may be desirable to purify a protein, for example, an ELP composition fusion protein. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide or polypeptide are filtration, ion-exchange chromatography, exclusion chromatography, polyacrylamide gel electrophoresis, affinity chromatography, or isoelectric focusing. A particularly efficient method of purifying peptides is fast protein liquid chromatography or even HPLC. In the case of ELP compositions protein purification may also be aided by the thermal transition properties of the ELP domain as described in U.S. Pat. No. 6,852,834.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulfate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/

PAGE (Capaldi et al., 1977). It will therefore be appreciated that under differing electrophoresis conditions, the apparent molecular weights of purified or partially purified expression products may vary.

B. Antibodies

Another embodiment of the present invention may involve antibodies. In some cases, for example an antibody may be used a cell targeting domain in a ELP composition of the invention. Such antibodies may be made against virtually any antigen of interest according to methods that are well known to those in the art.

mAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified polypeptide, peptide or domain, be it a wild-type or mutant composition. The immunizing composition is administered in a manner effective to stimulate antibody producing cells.

Antibodies may be further purified, if desired, using filtration, centrifugation and various chromatographic methods such as HPLC or affinity chromatography. Fragments of the monoclonal antibodies of the invention can be obtained from the monoclonal antibodies so produced by methods which include digestion with enzymes, such as pepsin or papain, and/or by cleavage of disulfide bonds by chemical reduction. Alternatively, antibody fragments encompassed by the present invention can be synthesized using an automated peptide synthesizer.

It also is contemplated that a molecular cloning approach may be used to generate antibodies.

"Humanized" antibodies are also contemplated, as are chimeric antibodies from mouse, rat, or other species, bearing human constant and/or variable region domains, bispecific antibodies, recombinant and engineered antibodies and fragments thereof. The techniques for producing humanized immunoglobulins are well known to those of skill in the art. For example U.S. Pat. No. 5,693,762 discloses methods for producing, and compositions of, humanized immunoglobulins having one or more complementarity determining regions (CDR's). When combined into an intact antibody, the humanized immunoglobulins are substantially non immunogenic in humans and retain substantially the same affinity as the donor immunoglobulin to the antigen, such as a protein or other compound containing an epitope. Examples of other teachings in this area include U.S. Pat. Nos. 6,054,297; 5,861,155; and 6,020,192, all specifically incorporated by reference. Methods for the development of antibodies that are "custom-tailored" to the patient's disease are likewise known and such custom-tailored antibodies are also contemplated.

III. THERAPEUTIC AND PREVENTATIVE METHODS

A. Pharmaceutical Formulations, Delivery, and Treatment Regimens

In certain embodiments of the invention, there are methods of achieving a therapeutic effect, such as treatment of a disease by ELP delivery of therapeutic compositions such as nucleic acids.

An effective amount of the pharmaceutical composition, generally, is defined as that amount sufficient to detectably and repeatedly to ameliorate, reduce, minimize or limit the extent of the disease or its symptoms. More rigorous definitions may apply, including elimination, eradication or cure of disease.

To effect a physiological or therapeutic effect using the methods and compositions of the present invention, one would generally contact a cell with the therapeutic compound or candidate therapeutic agent, such as a protein or an expression construct encoding a protein. The routes of administration will vary, naturally, with the location and nature of the lesion, and include, e.g., intradermal, transdermal, parenteral, intravenous, intramuscular, intranasal, subcutaneous, percutaneous, intratracheal, intraperitoneal, intratumoral, perfusion, lavage, via inhalation (e.g., as an aerosol), direct injection, and oral administration and formulation.

For example, in the case where a bioplex of the invention is administered as an aerosol the unique thermal transition properties conferred by the ELP domain may offer certain therapeutic advantages. For example, a bioplex may be dispersed in a liquid prior to administration (e.g., at a temperature below the transition temperature for the bioplex). Then for administration temperature may be raised during or prior to aerosolization, thereby enabling methods for adjusting the size of aerosol particulates based on the magnitude of the temperature increase. Thus, methods for delivery of therapeutics (e.g., nucleic acids) via inhaled bioplexes may be far more efficient than prior methods that do not allow for the modulation of the delivery particle size.

To effect a therapeutic benefit with respect to a genetic disease, condition, or disorder, one would contact a cell having the relevant nucleic acids and exhibiting the unwanted phenotype with the therapeutic compound. Any of the formulations and routes of administration discussed with respect to the treatment or diagnosis of cancer may also be employed with respect to such diseases and conditions.

Continuous administration also may be applied where appropriate. Delivery via syringe or catherization is preferred. Such continuous perfusion may take place for a period from about 1-2 hours, to about 2-6 hours, to about 6-12 hours, to about 12-24 hours, to about 1-2 days, to about 1-2 wk or longer following the initiation of treatment. Generally, the dose of the therapeutic composition via continuous perfusion will be equivalent to that given by a single or multiple injections, adjusted over a period of time during which the perfusion occurs. It is further contemplated that limb perfusion may be used to administer therapeutic compositions of the present invention.

Treatment regimens may vary as well, and often depend on disease progression, and health and age of the patient. Obviously, certain conditions, disorders, or diseases will require more aggressive treatment, while at the same time, certain patients cannot tolerate more taxing protocols. The clinician will be best suited to make such decisions based on the known efficacy and toxicity (if any) of the therapeutic formulations.

The treatments may include various “unit doses.” Unit dose is defined as containing a predetermined quantity of the therapeutic composition. The quantity to be administered, and the particular route and formulation, are within the skill of those in the clinical arts. A unit dose need not be administered as a single injection but may comprise continuous infusion over a set period of time. Unit dose of the present invention may conveniently be described in terms of, for example, mg or μg amounts of ELP composition.

It is specifically contemplated that the candidate substance, candidate therapeutic agent, or ELP is administered to the subject over a period of time of about, of at least about, or at most about 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96 hours or more, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90 days or more, 1, 2, 3, 4, 5, 6, 7, 8, 9, 10, 11, 12 weeks or more, 1, 2, 3, 4 months or more, or any range derivable therein.

In other embodiments, methods involve administering a dose or dosage of a compound or agent to the subject. It will be understood that the amount given to the subject may be dependent on the weight of the subject and this may be reflected in the amount given in a day (e.g., a 24-hour period). In some embodiments, a subject is given about, less than about, or at most about 0.005, 0.05, 0.1, 0.2, 0.3, 0.4, 0.5, 0.6, 0.7, 0.8, 0.9, 1.0, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 100, 110, 120, 130, 140, 150 nM/kg/day, or any range derivable therein. Alternatively, the amount of compound or agent that is administered can be expressed in terms of nanogram (ng). In certain embodiments, the amount given is about, less than about, or at most about 0.005, 0.05, 0.1, 0.2, 0.3, 0.4, 0.5, 0.6, 0.7, 0.8, 0.9, 1.0, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 ng/kg/day, or any range derivable therein.

B. Injectable Compositions and Formulations

Pharmaceutical compositions disclosed herein may alternatively be administered parenterally, intravenously, intradermally, intramuscularly, transdermally or even intraperitoneally as described in U.S. Pat. No. 5,543,158; U.S. Pat. No. 5,641,515 and U.S. Pat. No. 5,399,363 (each specifically incorporated herein by reference in its entirety).

Injection of nucleic acid, small molecules, or proteins may be delivered by syringe or any other method used for injection of a solution, as long as the expression construct can pass through the particular gauge of needle required for injection. A novel needleless injection system has recently been described (U.S. Pat. No. 5,846,233) having a nozzle defining an ampule chamber for holding the solution and an energy device for pushing the solution out of the nozzle to the site of delivery. A syringe system has also been described for use in gene therapy that permits multiple injections of predetermined quantities of a solution precisely at any depth (U.S. Pat. No. 5,846,225).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intratumoral and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

In certain embodiments, the agent or substance may be administered to the subject in prodrug form, meaning that it will become the active agent or substance once it has entered the subject's body, or a certain body cavity or cell.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" or "pharmacologically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared.

In certain embodiments, the present invention concerns compositions comprising one or more lipids associated with a nucleic acid, an amino acid molecule, such as a peptide, or another small molecule compound. A lipid is a substance that is characteristically insoluble in water and extractable with an organic solvent. Compounds than those specifically described herein are understood by one of skill in the art as lipids, and are encompassed by the compositions and methods of the present invention. A lipid component and a non-lipid may be attached to one another, either covalently or non-covalently.

It is contemplated that a liposome/Fortilin modulator composition may comprise additional materials for delivery to a tissue. For example, in certain embodiments of the invention, the lipid or liposome may be associated with a hemagglutinating virus (HVJ). This has been shown to facilitate fusion with the cell membrane and promote cell entry of liposome-encapsulated DNA (Kaneda et al., 1989). In another example, the lipid or liposome may be complexed or employed in conjunction with nuclear non-histone chromosomal proteins (HMG-1) (Kato et al., 1991). In yet further embodiments, the lipid may be complexed or employed in conjunction with both HVJ and HMG-1.

C. Hyperthermia Therapy

The in vitro and in vivo uses of hyperthermia include several effects (both beneficial and detrimental) that should be addressed prior to application of therapy. Hyperthermia has long been used for the treatment of cancer; moreover, several studies show promising synergistic effects of hyperthermia combined with chemo- and/or radiotherapy. For example, 43° C. hyperthermia has been shown to increase the thermal enhancement ratio (TER, ratio of cell viability with hyperthermia to co-administered hyperthermia and drug) of Cisplatin by ~1.4-5.0 fold in mouse mammary tumors (Beketic-Oreskovic et al., 1997). While it is apparent that hyperthermia can induce cancer cell death at T>43° C., Hsp activation has been shown to convert some cells to a hyperthermia-insensitive or "thermotolerant" state, effectively ending the hyperthermic apoptotic pathway (Hildebrandt et al., 2002).

Inducing hyperthermia in accordance with the methods of the present invention can be accomplished in a variety of manners. Essentially any technique that produces an appropriate increase in temperature in the tissue of interest can be used. Preferably, techniques of raising temperature in tissue that allow for maintaining the elevated temperature over a period of time are used.

Several methods of inducing hyperthermia in tissue have been described. U.S. Pat. No. 6,167,313 provides an overview of several techniques and methods. Any standard technique can be used to accomplish the desired hyperthermia. For example, an ultrasonic transducer can be employed to deliver a localized increase in tissue temperature. For an example of methods and apparatuses in accordance with this category, see U.S. Pat. No. 5,620,479. Alternatively, a technique commonly referred to as interstitial hyperthermia can be employed. Other alternative methods of inducing hyperthermia include exposing the tissue to microwave radiation (for example, see U.S. Pat. No. 5,861,021 and U.S. Pat. No. 5,922,013) or magnetic induction (see U.S. Pat. No. 6,167,313).

The method employed to induce hyperthermia can be optimized based upon the nature of the tissue of interest. For example, for deep tissues, such as a tumor in prostate tissue, interstitial hyperthermia will likely offer a better ability to control the hyperthermia. For surface tissues, a simple device, such as an ultrasonic transducer, will likely by sufficient.

D. Additional Combination Treatments

Administration of the therapeutic agent or substance of the present invention to a patient will follow general protocols for the administration of that particular secondary therapy, taking into account the toxicity, if any, of the treatment. It is expected that the treatment cycles would be repeated as necessary. It also is contemplated that various standard therapies, as well as surgical intervention, may be applied in combination with the described therapy.

IV. EXAMPLES

The following examples are included to further illustrate various aspects of the invention. It should be appreciated by those of skill in the art that the techniques disclosed in the examples that follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Construction of ELP Compositions

Construction of a nucleic acid binding domain. Initially, oligonucleotides are designed such that the EcoR I, HinD III, PflM I, and Bgl I restriction sites were conserved in the coding backbone to facilitate DNA oligomerization by seamless recursive directional ligation (SRDL). The initial $(VKG)_4$ DNA sequences, forward and reverse respectively are as follows: 5'-aattcccacggcgtggttaaaggtgttaaaggtgttaaagg tgttaaagtgccgggcgggca-3' (SEQ ID NO:2) and 5'-agcttgcccgc-ccggcactttaacacctttaacacctttaacacctttaaccacgccgtggg-3' (SEQ ID NO:3). The oligonucleotides are annealed by heating an equimolar mixture of the two oligonucleotides at 95° C. for 5 min and then slowly cooling to room temperature to form a double-stranded DNA cassette with EcoR I and HinD III compatible ends. pUC19 is doubly digested with EcoR I and HinD III and enzymatically dephosphorylated using calf alykline phosphotase (CIP). The linearized pUC19 vector is purified from high-melt agarose gel extraction using a spin column purification kit and eluted. The annealed oligonucleotides and linearized vector are ligated by incubating with T-4 ligase in 20 μl ligase buffer at 16° C. for 5 h. The ligation mixture is combined with 100 μl of chemically competent Top10 cells, transformed by traditional heat shock method, spread on CircleGrow medium agar plates supplemented with ampicillin (100 μg/ml), and incubated overnight at 37° C. Multiple colonies are chosen and grown in 5 mL CircleGrow medium for 12 hrs at 37° C. Plasmids are isolated and purified from the 5 mL cultures using a QIAGEN Miniprep kit. DNA sequencing and a diagnostic digest of the purified plasmids using EcoR I and HinD III were performed to screen the clone containing the putative insert.

SRDL DNA oligomerization of $(VKG)_{4a}$. To generate $(VKG)_{4a}$, where a=1-4, the gene for the $(VKG)_4$ tripeptide unit is used as the starting monomer unit and SRDL oligomerization is performed. The vector containing a gene for $(VKG)_4$ is linearized with PflM I, dephosphorylated with CIP, and separated on an agarose gel. The linearized plasmid is purified from the gel using a spin column purification kit. A separate sample of vector is doubly digested with PflM I and Bgl I to liberate the gene encoding $(VKG)_4$ monomer. After digestion, the reaction products are separated on an agarose gel by electrophoresis, and the insert is purified from the gel using a DNA extraction kit. The purified insert is ligated into the linearized vector, and the resulting plasmid is transformed into *E. coli* Top10 cells. Transformants are initially screened by diagnostic digestion using EcoR I and HinD III and further confirmed by DNA sequencing. A clone containing a gene for $(VKG)_8$ peptide is identified and selected for next round of RDL. Additional rounds proceed identically using the plasmids of previous rounds as the starting clones.

Construction of (VKG)4aELP gene cloning library. The vector containing a copy of the gene of ELP1 is linearized with PflM I, dephosphorylated with CIP, and separated on an agarose gel. The linearized plasmid is purified from the gel using a spin DNA extraction kit. The separate pUC19 vector containing $(VKG)_{4a}$ gene is doubly digested with PflM I and Bgl I to liberate the insert. After digestion, the reaction products are separated on an agarose gel by electrophoresis, and the insert is purified from the gel using a DNA extraction kit. The purified insert and linearized vector are ligated. The ligation mixture is transformed into *E. coli* Top10 cells and the transformants are screened using the protocol described above. The desired clones initially are identified by diagnostic digestion with EcoR I and HindD III and further confirmed by DNA sequencing.

Construction of (VKG)4aELP copolymer expression library. The pUC19-based cloning vector containing the gene encoding $(VKG)_{4a}$ELP copolymer is digested with PflM I and Bgl I, and the gene cassette is separated from the pUC19 vector fragments on an agarose gel by electrophoresis, and then purified from the gel. The pET-25b(+)SV2 vector is linealrized by digestion with Sfi I, enzymatically dephosphorylated with CIP, and then purified by agarose gel extraction following electrophoresis. The purified insert and the linearized vector were ligated, and the ligation mixture was transformed into *E. coli* Top10 cells. Plasmids isolated from the resulting transformants are screened by diagnostic digestion with Ava I and Xba I, and the identity of insert was then further confirmed by DNA sequencing. The plasmid containing correct insert gene was transformed into *E. coli* BLR (DE3) strain by heat shock method.

Expression and purification of cationic ELP compositions (diblock copolymers). The $(VKG)_{4a}$ELP diblock copolymers are expressed in *E. coli* BLR(DE3) using a noninduced expression protocol and purified from the soluble cell lysate according to the inverse transition cycling (ITC) protocol. The concentration of ELP solutions is determined by UV spectrophotometry using a molar extinction coefficient of 5690 $M^{-1}$ $cm^{-1}$ at 280 nm Example 2

ELP Composition—Nucleic Acid Complexes

Various amounts of cationic $(VKG)_{16}$ELP1-90 in PBS were mixed with 1 μg of hsp-EGFP plasmid DNA to obtain a desired N/P ratio ranging from 0.1 to 1.0. Total volume of reaction mixture was adjusted to 30 μl. After incubation on ice for 45 min, 15 μl of reaction mixture (equivalent to 500 ng of hsp-EGFP plasmid DNA) was analyzed by agarose gel electrophoresis.

Figure 2:
FIG. 2: A gel Retardation assay. Lane 1 shows mobility of linear (a) and super-coiled (c) forms of hsp-EGFP plasmid in the absence of $(VKG)_{16}ELP1$-90. Lane 2, 3, 4, 5, 6, 7, 8, and 9 represent the mixtures of $(VKG)_{16}ELP1$-90 and hsp-EGFP plasmid at the N/P ratio of 0.05, 0.075, 0.1, 0.2, 0.3, 0.4, 0.5 and 1.0, respectively.

DNA mobility retardation assay for the analysis of complex formation between $(VKG)_{16}$ELP1-90 and hsp-EGFP plasmid. Electrophoresis was performed at 100 V for 60 min on a 1.0% high melting agarose gel and visualized by ethidium bromide staining (FIG. 2). Lane MW shows size standards with base pairs of 8454, 7242, 6369, 5686, 4822, 4324, 3675, 2323 and 1929. Lane 1 shows mobility of linear (a) and super-coiled (c) forms of hsp-EGFP plasmid in the absence of $(VKG)_{16}$ELP1-90. Lane 2, 3, 4, 5, 6, 7, 8, and 9 represent the mixtures of $(VKG)_{16}$ELP1-90 and hsp-EGFP plasmid at the N/P ratio of 0.05, 0.075, 0.1, 0.2, 0.3, 0.4, 0.5 and 1.0, respectively. Complete retardation of hsp-EGFP plasmid was observed at 1:1 N/P ratio of $(VKG)_{16}$ELP1-90: hsp-EGFP plasmid. Lane 10 represent the sample from the mixture of ELP1-90 (168 μg) and hsp-EGFP plasmid (1.0 μg), demonstrating that ELP1-90 does not bind DNA. Each lane contains 500 ng of hsp-EGFP DNA.

Example 3

Thermal Transition Properties of ELP-Nucleic Acid Complexes

To characterize the inverse temperature transition of $(VKG)_{4a}$ELP copolymer and $(VKG)_{4a}$ELP/pDNA polyplexes, the optical density of sample solutions (typically 25, 12.5 or 6.25 μM of copolymer in PBS) is monitored at 350 nm as a function of temperature on a Cary 300 UV-visible spectrophotometer equipped with a multicell thermoelectric temperature controller (Cary Instruments, Walnut Creek, Calif.). The heating and cooling rates are 1° C. $min^{-1}$. The derivative of the turbidity profile with respect to temperature is numerically calculated, and the Tt value is defined as the temperature at which the increase in turbidity is most rapid. Particale size is also determined by dynamic light scattering using a Zeta-Plus, BI MAS Option (Brookhaven Instruments Corporation, Holtsville, N.Y.) (Table 5).

Figure 3:
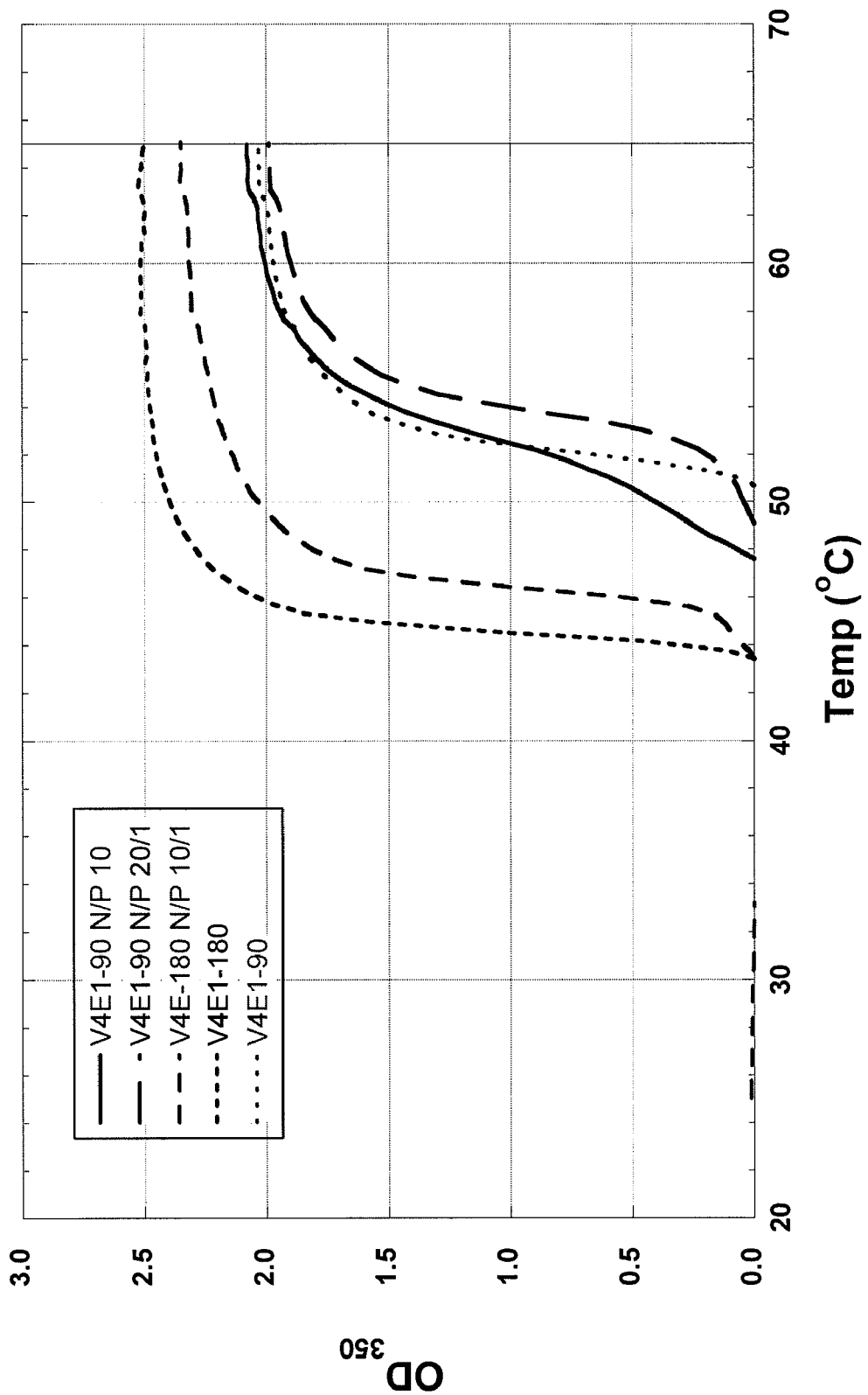
FIG. 3: Thermal transition profiles for $(VKG)_4ELP1$-90/pDNA bioplexes N/P ratios are indicated on the left.

As the N/P ratio of decreases from 10 to 1, the Tt of polyplex decreases (FIGS. 3-5). At the N/P ratio of 1, the turbidity profiles shows a sharp phase transition with a single Tt value, suggesting stoichiometric formation of bioplex (data summarized in Table. The transition profile of the ELP/pDNA bioplexes is superimposable with that of uncomplexed, free ELP. The turbidity profiles of ELP/pDNA complexes are reversible and reproducible. When the solution temperature is cooled down to 25° C. after 1st round of thermal transition, the solution is again optically transparent. When repetitive experiments with the same sample are performed, the turbidity profile obtained for the 2nd round thermal transition is almost identical to that of the $1^{st}$ round thermal transition. The result suggests that the Tt values and the pattern of transition profile represent distinctive thermosensitivity of each ELP/pDNA polyplex. The (VKG)$_8$ELP 1-20/pDNA and (VKG)$_8$ELP1-180/pDNA polyplexes prove the concept of thermally targeted gene delivery; they are soluble at normal body temperature (37° C.), however efficiently precipitate at the temperature of local hyperthermia (42-43° C.).

TABLE 5

| (VKG)$_{4a}$ELP | $T_t$ (° C.)[a] | | Particle size of micelles (nm)[b] |
|---|---|---|---|
| | Free (VKG)$_{4a}$ELP | (VKG)$_{4a}$ELP1/ DNA Micelle | |
| (VKG)$_8$ELP1-120 | 50.4 ± 2.7 | 41.1 ± 1.7 | 58.0 ± 1.6 |
| (VKG)$_8$ELP1-180 | 44.0 ± 2.1 | 38.9 ± 2.5 | 67.4 ± 17.2 |
| (VKG)$_{16}$ELP1-180 | 46.5 ± 1.9 | 31.5 ± 1.6 | 112.3 ± 13.3 |

[a]Samples were normalized to 6.25 μM cationic ELP concentration and an N/P ratio 1.
[b]Samples were normalized to 12.5 μM cationic ELP concentration and an N/P ratio 1. (In each case data is reported as mean ± SD, n = 3).

Example 4

Determination of Bioplex Particle Size and Morphology

Cationic ELP diblock copolymer stock solutions (10-20 mg/ml) are prepared by dissolving biopolmers in sterile PBS of pH 7.25. The pDNA solutions (1-2 mg/ml) are prepared by dissolving the DNA in the same PBS. Cationic ELP/pDNA nanobioplexes are prepared by adding the DNA (300 ml) to the biopolymer solution followed by intense stirring on vortex mixer for 10 seconds. The resultant solutions are allowed to stand for 10 hrs min at 25° C. No precipitation is observed during complexation. Size determination by dynamic light scattering was carried out using a (Hialeah, Fla.) submicron particle analyzer (model N4).

Transmission electron microscopy. The (VKG)$_8$ELP1-120/pDNA polyplex are prepared at 12.5 μM polymer concentration and N/P ratio of 1. Five microliter of complexes are loaded on the Cu grid for 2 min followed by blotting of the excess liquid and incubation for another 2 min with 2% methylamine tungstate followed by blotting. The grid is air-dried for another 2 min and visualized under the electron microscope. Digital images are captured using the instrument software.

Figure 6:
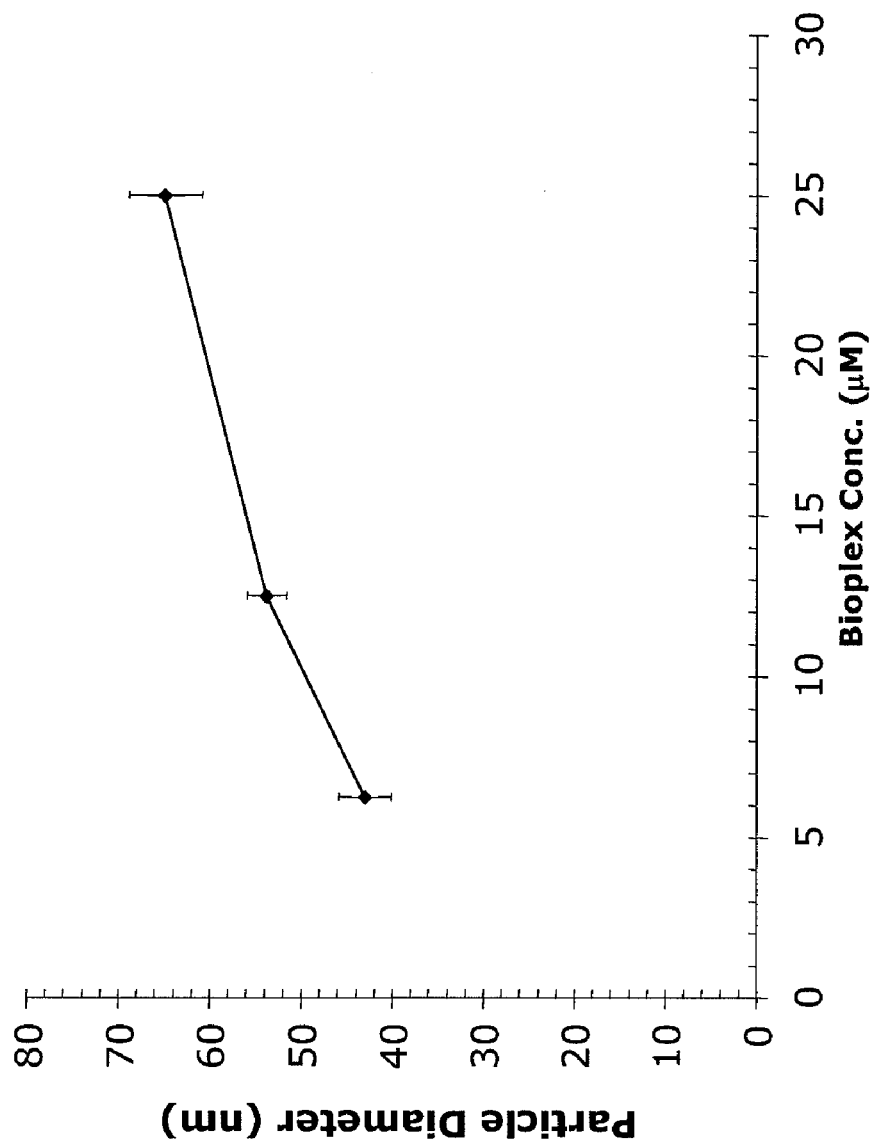
FIG. 6: Dynamic light scattering analysis of $(VKG)_8$-ELP1-120/pDNA bioplex particle size as a function of concentration.

The particle sizes of the ELP/pDNA polyplex are measured by dynamic light scattering (DLS). The particle sizes of polyplexes are smaller than 150 nm under the condition studied here. The morphology of the (VKG)8-ELP1-120/pDNA bioplex was observed at magnifications of 175,000 by transmission electron microscopy and it appeared as an oval shape particles with an average of size of 35 nm (FIG. 6), which corresponds to particle size measured by DLS. From the viewpoints of size and origin of the cationic ELP diblock polymers, we call ELP/pDNA complex a nanobioplex.

Example 5

Nucleic Acid Release from Bioplexes

It has been proposed that an exchange reaction with negatively charged biomacromolecules would be a major mechanism of pDNA release from polyplex for efficient transcription of loaded pDNA in the in a target cells. In this regard, we monitored release of pDNA from ELP/pDNA nanobioplex at physiological pH by using poly(aspartic acid) as a model polyanion. As shown in FIG. 7A-B, pDNA was released from both (VKG)$_8$ELP1-120/pDNA and (VKG)$_8$ELP1-180/pDNA nanobioplexes due to the exchange reaction with poly (aspartic acid). The Fig also shows that the ratio of the intensity of open-circular DNA to supercoiled DNA is increased, indicating the pDNA released from polyplexes is more relaxed in conformation compared to native pDNA.

Nucleic acid dissociation by a counter polyelectrolyte is encouraging; however, to demonstrate that hyperthermia destabilizes ELP/DNA PIC micelles by hydrophobic collapse of the ELP corona and subsequent expulsion of the DNA cargo, a hyperthermic release assay was completed (FIG. 7C). Since (VKG)$_8$-ELP1-120/DNA polyplexes demonstrate a Tt of ~40° C. (i.e., at a N/P <1) the cationic elastin diblock copolymers hydrophobically collapse (T>Tt) thereby limiting the amount of available cationic charge for DNA condensation and subsequent retardation. At N/P <1 longer DNA migration is expected since the PIC micelles are not fully condensed. At N/P 1 the complexes show condensed DNA (FIG. 2), stable/monodisperse particles, and thermosensitivity at 40° C. (Table 5). It is interesting to note the parabolic flow profile with the N/P 1 bands in FIG. 7C of the hyperthermic gel, perhaps a consequence of the cationic elastin diblock copolymers retarding flow slightly. As expected, with increasing N/P ratios (increasing cationic copolymer), the DNA migration and/or release is minimal.

Example 6

Nucleic Acid Delivery with ELP Compositions

Figure 8:
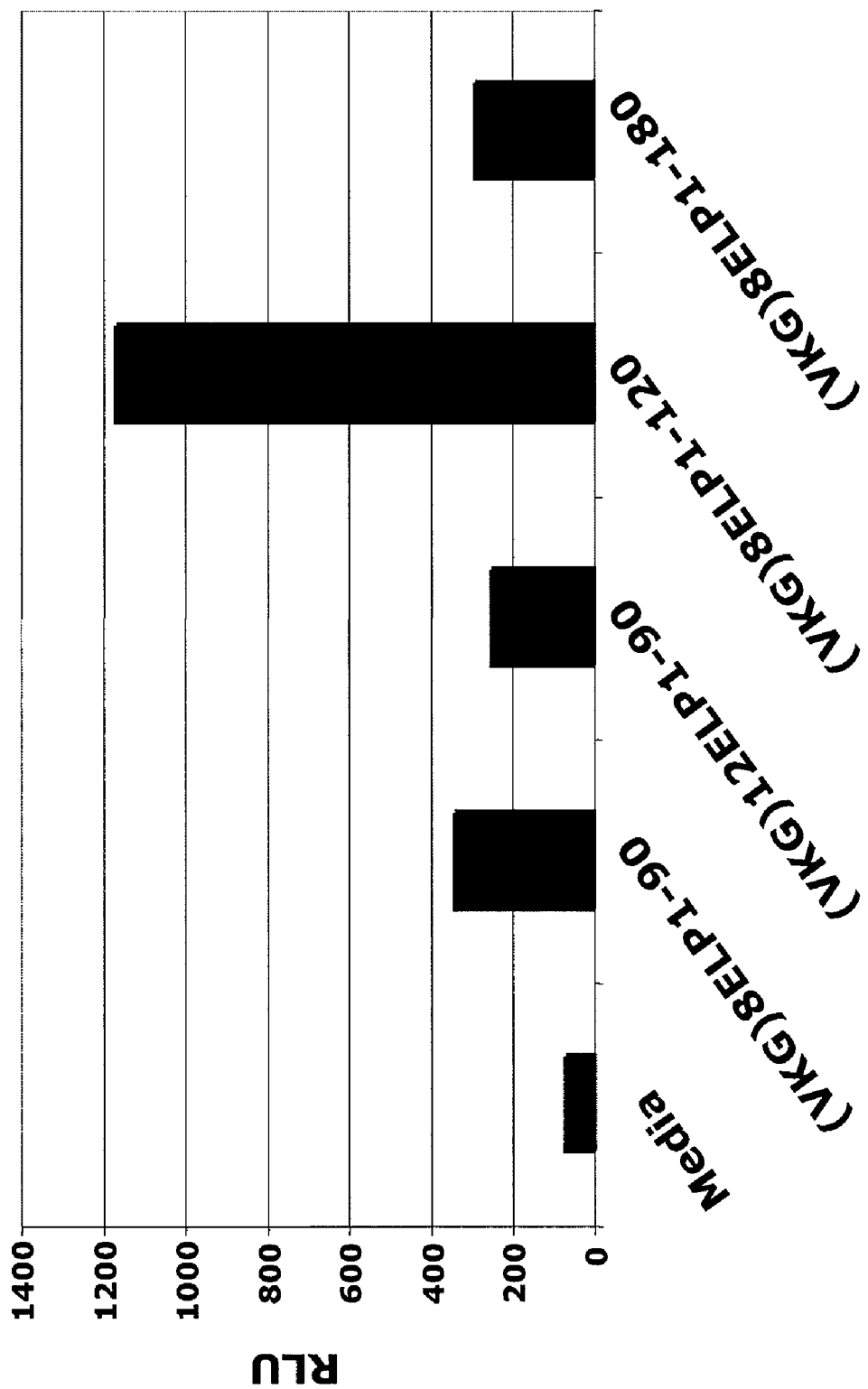
FIG. 8: Bioplex/pLuc transfection of MDA-MB-231 cells in media with 10% FBS. X axis indicated the bioplex used for transfection ("media" indicates the negative control). Y axis indicates luciferase activity in transfected cells expressed as relative light units (RLU).

Bioplexes comprising a luciferase expression plasmid are used to transfect MDA-MB-231 cells in media with 10% FBS. Successful bioplex transfection is detected by luciferase assays form cell lysates (FIG. 8).

Example 7

Transition Properties of (VKG)4a-ELP(1-90)

TABLE 6

Characteristics of ELP(1-90) Homopolymer and the (VKG)4a-ELP(1-90) Block Copolymers (a = 1, 2, 3 and 4)

| composition | pI[a] | MW[a] (Da) | cationic block contents[b] (%) | $T_t$ (° C.) |
|---|---|---|---|---|
| ELP(1-90) | 7.98 | 35,231 | 0 | 42.2 |
| (VKG)$_4$-ELP(1-90) | 11.0 | 36,621 | 3.8 | 44.9 |
| (VKG)$_8$-ELP(1-90) | 11.2 | 38,012 | 7.4 | 47.2 |
| (VKG)$_{12}$-ELP(1-90) | 11.3 | 39,403 | 10.6 | 50.4 |
| (VKG)$_{16}$-ELP(1-90) | 11.4 | 40,794 | 13.7 | ND[c] |

[a]The theoretical pI (isoelectric point) was determined by using a compute pI/Mw tool (www.expasy.org/tools/pi_tool.html).
[b](MW of cationic block)/(MW of block copolymer) × 100.
[c]Not determined.

TABLE 7

Effects of polymer concentration on Tt of the (VKG)4a-ELP(1-90) block copolymers

| | composition | polymer concentration (μM) | | | | | | |
|---|---|---|---|---|---|---|---|---|
| | | 6.25 | 12.5 | 25 | 50 | 100 | 250 | 500 |
| $T_t$ (° C.) | (VKG)$_4$-ELP(1-90) | 51.8 | 48.7 | 46.1 | 44.6 | 43.1 | 41.2 | 39.8 |

TABLE 7-continued

Effects of polymer concentration on Tt of the (VKG)4a-ELP(1-90) block copolymers

| composition | polymer concentration (μM) | | | | | | |
|---|---|---|---|---|---|---|---|
| | 6.25 | 12.5 | 25 | 50 | 100 | 250 | 500 |
| (VKG)$_8$-ELP(1-90) | 51.1 | 49.7 | 48.4 | 47.6 | 45.1 | 43.2 | 40.8 |
| (VKG)$_{12}$-ELP(1-90) | 52.9 | 51.2 | 49.9 | 48.2 | 46.5 | 45.7 | 45.1 |
| (VKG)$_{16}$-ELP(1-90) | ND[a] | ND[a] | ND[a] | ND[a] | ND[a] | ND[a] | ND[a] |

[a]Not determined

TABLE 8

Effects of NaCl concentration on Tt of the (VKG)4a-ELP(1-90) block copolymers

| | composition | NaCl concentration (M) | | | | | |
|---|---|---|---|---|---|---|---|
| | | 0.05 | 0.1 | 0.3 | 0.5 | 1.0 | 2.0 |
| $T_t$ (° C.) | (VKG)$_4$-ELP(1-90) | 49.1 | 48.4 | 42.5 | 38.8 | 32.2 | 21.0 |
| | (VKG)$_8$-ELP(1-90) | 51.2 | 46.9 | 43.2 | 39.7 | 31.9 | 19.9 |
| | (VKG)$_{12}$-ELP(1-90) | ND[a] | 49.2 | 45.4 | 41.6 | 32.9 | 18.0 |
| | (VKG)$_{16}$-ELP(1-90) | ND[a] | ND[a] | 44.8 | 41.7 | 32.7 | 18.0 |

[a]Not determined

TABLE 9

Effects of pH on Tt of the (VKG)4a-ELP(1-90) block copolymers

| | composition | pH | | | | | | |
|---|---|---|---|---|---|---|---|---|
| | | 6.0 | 7.0 | 8.0 | 9.0 | 10.0 | 11.0 | 12.0 |
| $T_t$ (° C.) | (VKG)$_4$-ELP(1-90) | 44.1 | 44.5 | 45.4 | 46.6 | 50.5 | 48.6 | 47.6 |
| | (VKG)$_8$-ELP(1-90) | 47.3 | 47.0 | 48.2 | 48.9 | 52.1 | 47.8 | 47.7 |
| | (VKG)$_{12}$-ELP(1-90) | 50.0 | 49.6 | 50.1 | 50.2 | 50.2 | 53.7 | 46.9 |
| | (VKG)$_{16}$-ELP(1-90) | ND[a] | ND[a] | ND[a] | ND[a] | ND[a] | ND[a] | 47.7 |

[a]Not determined

V. REFERENCES

The following references, to the extent that they provide exemplary procedural or other details supplementary to those set forth herein, are specifically incorporated herein by reference.

U.S. Pat. No. 4,196,265
U.S. Pat. No. 4,554,101
U.S. Pat. No. 4,683,202
U.S. Pat. No. 5,354,855
U.S. Pat. No. 5,466,468
U.S. Pat. No. 5,620,479
U.S. Pat. No. 5,693,762
U.S. Pat. No. 5,846,225
U.S. Pat. No. 5,846,233
U.S. Pat. No. 5,861,021
U.S. Pat. No. 5,861,155
U.S. Pat. No. 5,922,013
U.S. Pat. No. 5,928,906
U.S. Pat. No. 6,020,192
U.S. Pat. No. 6,054,297
U.S. Pat. No. 6,167,313
U.S. Pat. No. 6,852,834
U.S. Publn. 20030059944
U.S. Publn. 20030105051
Ausubel et al., In: *Current Protocols in Molecular Biology*, John, Wiley & Sons, Inc, New York, 1996.
Beketic-Oreskovic et al., *Int. J. Hyperthermia*, 13(2):205-214, 1997.
Berzal-Herranz et al., *Genes Dev*, 6(1):129-134, 1992.
Bidwell and Raucher, *Mol. Cancer. Ther.*, 4(7):1076-1085, 2005.
Braiden et al., *Hum. Gene Ther.*, 11(18):2453-2463, 2000.
Brummelkamp et al., *Science*, 296(5567):550-553, 2002.
Capaldi et al., *Biochem. Biophys. Res. Comm.*, 74(2):425-433, 1977.
Cech et al., *Cell*, 27(3 Pt 2):487-496, 1981.
Chowrira et al., *J. Biol. Chem.*, 268:19458-62, 1993.
Chowrira et al., *J. Biol. Chem.*, 269(41):25856-25864, 1994.
Dreher et al., *J Control Release*, 91(1-2):31-43, 2003.
Elbashir et al., *Genes Dev.*, 5(2):188-200, 2001.
Forster and Symons, *Cell*, 49(2):211-220, 1987.
Gerlach et al., *Nature* (London), 328:802-805, 1987.
Harlow and Lane, In: *Antibodies, a Laboratory Manual*, Cold Spring Harbor Laboratory, 139-281, 1988.
Haseloff and Gerlach, *Nature*, 334(6183):585-591, 1988.
Herrero-Vanrell et al., *J. Control Release*, 102(1):113-122, 2005.
Hildebrandt et al., *Crit. Rev. Oncol. Hematol.*, 43(1):33-56, 2002.
Johnson et al., In: *Biotechnology And Pharmacy*, Pezzuto et al. (Eds.), Chapman and Hall, N.Y., 1993.
Joyce, *Nature*, 338:217-244, 1989.
Kaneda et al., *Science*, 243:375-378, 1989.
Kato et al, *J. Biol. Chem.*, 266:3361-3364, 1991.
Kim and Cech, *Proc. Natl. Acad. Sci. USA*, 84(24):8788-92, 1987.
Kim et al., *J. Biomed. Mater Res. A*, 70(1):154-158, 2004.
Kopecek, *Eur. J. Pharm. Sci.*, 20(1):1-16, 2003.
Kyte and Doolittle, *J. Mol. Biol.*, 157(1):105-132, 1982.
Lieber and Strauss, *Mol. Cell. Biol.*, 15(1):540-551, 1995.
Michel and Westhof, *J. Mol. Biol.*, 216:585-610, 1990.
Palukaitis et al., *Virology*, 99:145-151, 1979.
Parker et al., *Anal. Biochem.*, 302(1):75-80, 2002.
PCT Appln. WO 03/012052
Perriman et al., *Gene*, 113:157-163, 1992.
Perrotta and Been, *Biochemistry*, 31(1):16-21, 1992.
Prody et al., *Science*, 231:1577-1580, 1986.
Reinhold-Hurek and Shub, *Nature*, 357:173-176, 1992.
Remington's Pharmaceutical Sciences" 15th Edition, pages 1035-1038 and 1570-1580, 1990.
Sambrook et al., In: *Molecular cloning: a laboratory manual*, 2$^{nd}$ Ed., Cold Spring Harbor Laboratory Press, Cold Spring Harbor, N.Y., 1989.
Sarver et al., *Science*, 247:1222-1225, 1990.
Scanlon et al., *Proc. Natl. Acad. Sci. USA*, 88:10591-10595, 1991.
Schild, *Prog. Polymer Sci.*, 17(2):163-249, 1992.
Sioud et al., *J. Mol. Biol.*, 223:831-835, 1992.
Sosnik and Cohn, *Biomaterials*, 26(4):349-357, 2005.
Sui et al., *Proc. Natl. Acad. Sci. USA*, 99(8):5515-5520, 2002.
Symons, *Annu. Rev. Biochem.*, 61:641-671, 1992.
Symons, *Nucl. Acids Res.*, 9(23):6527-6537, 1981.
Thompson et al., *Nature Genet.*, 9:444-450, 1995.
Urry et al., *J Bioact. Compat. Polym.*, 6(3):263-282, 1991.
Yamauchi et al., *Macromolecules*, 37(10):3519-3522, 2004.
Yuan and Altman, *Science*, 263:1269-1273, 1994.
Yuan et al., *Proc. Natl. Acad. Sci. USA*, 89:8006-8010, 1992.

What is claimed is:

1. A bioplex composition comprising a therapeutic nucleic acid in complex with a fusion protein wherein the fusion protein comprises an elastin-like repeat and a nucleotide binding sequence, wherein the nucleic acid binding sequence comprises 4 to 100 repeats of the sequence VK or 4 to 100 repeats the sequence VKG.

2. The bioplex of claim 1, wherein the fusion protein further comprises a spacer region between the elastin-like repeat and a nucleotide binding sequence.

3. The bioplex of claim 1, wherein the elastin-like repeat comprises 10 to 500 repeats of the sequence VPGXG (SEQ ID NO:1) wherein X is any amino acid except proline.

4. The bioplex of claim 3, wherein X is valine, alanine or glycine.

5. The bioplex of claim 1, wherein the nucleic acid binding sequence comprises 4 to 100 repeats of the sequence VKG.

6. The bioplex of claim 1, wherein the nucleic acid binding sequence comprises 4 to 100 repeats of the sequence VK.

7. The bioplex of claim 5, wherein the fusion protein further comprises a spacer region between the elastin-like repeat and a nucleotide binding sequence.

8. The bioplex of claim 6, wherein the fusion protein further comprises a spacer region between the elastin-like repeat and a nucleotide binding sequence.

9. The bioplex of claim 2, wherein the spacer region comprises 3 or more histidine residues.

10. The bioplex of claim 1, wherein the fusion protein further comprises a cell targeting sequence, a cell penetrating sequence or a localization signal.

11. The bioplex of claim 2, wherein the spacer comprises a cleavable linker.

12. The bioplex of claim 11, wherein the cleavable linker is cleaved at low pH.

13. The bioplex of claim 11, wherein the cleavable linker is cleaved by an intracellular enzyme.

14. The bioplex of claim 1, wherein the bioplex has a median thermal transition temperature of less than about 48° C.

15. The bioplex of claim 1, wherein thermal transition of the bioplex occurs over a range of less than about 5° C.

16. The bioplex of claim 6, wherein the bioplex has an amino acid nitrogen to nucleic acid phosphate (N/P) ratio of less than about 50 to 1.

17. The bioplex of claim 1, wherein bioplex is less than about 1 μm in diameter.

18. The bioplex of claim 17, wherein bioplex is less than about 500 nm in diameter.

19. The bioplex of claim 18, wherein bioplex is less than about 200 nm in diameter.

20. The bioplex of claim 1, wherein the therapeutic nucleic acid is a DNA.

21. The bioplex of claim 20, wherein the DNA is a DNA expression vector.

22. The bioplex of claim 1, wherein the therapeutic nucleic acid is a RNA.

23. The bioplex of claim 22, wherein the RNA is a mRNA, a siRNA or a miRNA.

24. A method for delivery of a therapeutic nucleic acid to a cell comprising:
   i) mixing the therapeutic nucleic acid with a fusion protein comprising (a) an elastin-like repeat and (b) a nucleotide binding sequence comprising 4 to 100 repeats of the sequence VKG or 4 to 100 repeats of the sequence VK to form a bioplex; and
   ii) contacting the cell with the bioplex.

25. The method of claim 24, the method further comprising increasing the temperature around the bioplex after step ii).

26. The method of claim 25, wherein increasing the temperature around the bioplex decreases the aqueous solubility of the bioplex.

27. The method of claim 24, wherein the cell is in an animal.

28. The method of claim 25, wherein the animal is a human.

29. The method of claim 27, wherein the nanbioplex is administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, locally, by inhalation (e.g. aerosol inhalation), by injection, by infusion or by continuous infusion.

30. The method of claim 27, further comprising applying a hyperthermia therapy to the animal.

31. The method of claim 30, wherein the hyperthermia is applied locally.

32. The method of claim 31, wherein the hyperthermia therapy increases the local temperature to between about 38° C. and 46° C.

33. The method of claim 24, wherein the nucleic acid binding sequence comprises 4 to 100 repeats of the sequence VKG.

34. The method of claim 24, wherein the nucleic acid binding sequence comprises 4 to 100 repeats of the sequence VK.

35. The method of claim 33, wherein the fusion protein further comprises a spacer region between the elastin-like repeat and a nucleotide binding sequence.

36. The method of claim 34, wherein the fusion protein further comprises a spacer region between the elastin-like repeat and a nucleotide binding sequence.

* * * * *

UNITED STATES PATENT AND TRADEMARK OFFICE
CERTIFICATE OF CORRECTION

PATENT NO. : 8,367,626 B2
APPLICATION NO. : 11/747759
DATED : February 5, 2013
INVENTOR(S) : Darin Y. Furgeson and Younsoo Bae Page 1 of 1

It is certified that error appears in the above-identified patent and that said Letters Patent is hereby corrected as shown below:

In title page, item (57) Abstract, line 4, delete "of" and insert --or-- therefor.

In title page, item (57) Abstract, line 5, after "can" insert --be--.

In the Claims

In claim 16, column 38, line 17, delete "claim 6" and insert --claim 8-- therefor.

In claim 28, column 39, line 24, delete "claim 25" and insert --claim 27-- therefor.

In claim 32, column 40, line 14, delete the first occurrence of "C." and insert --C-- therefor.

Signed and Sealed this
Twenty-fourth Day of September, 2013

Teresa Stanek Rea
*Deputy Director of the United States Patent and Trademark Office*

SEQUENCE LISTING

```
<160> NUMBER OF SEQ ID NOS: 3

<210> SEQ ID NO 1
<211> LENGTH: 5
<212> TYPE: PRT
<213> ORGANISM: Artificial
<220> FEATURE:
<223> OTHER INFORMATION: Synthetic peptide
<220> FEATURE:
<221> NAME/KEY: XAA
<222> LOCATION: (4)..(4)
<223> OTHER INFORMATION: Any amino acid except proline.

<400> SEQUENCE: 1

Val Pro Gly Xaa Gly
1               5

<210> SEQ ID NO 2
<211> LENGTH: 62
<212> TYPE: DNA
<213> ORGANISM: Artificial
<220> FEATURE:
<223> OTHER INFORMATION: Synthetic primer

<400> SEQUENCE: 2
aattcccacg gcgtggttaa aggtgttaaa ggtgttaaag gtgttaaagt gccgggcggg      60
ca                                                                    62

<210> SEQ ID NO 3
<211> LENGTH: 62
<212> TYPE: DNA
<213> ORGANISM: Artificial
<220> FEATURE:
<223> OTHER INFORMATION: Synthetic primer

<400> SEQUENCE: 3
agcttgcccg cccggcactt taacaccttt aacacctttta acacctttaa ccacgccgtg      60
gg                                                                    62
```